(12) United States Patent
Kawano et al.

(10) Patent No.: US 10,595,717 B2
(45) Date of Patent: Mar. 24, 2020

(54) CAPSULE ENDOSCOPE SYSTEM AND MAGNETIC FIELD GENERATING DEVICE

(71) Applicant: OLYMPUS CORPORATION, Tokyo (JP)

(72) Inventors: Hironao Kawano, Machida (JP); Hironobu Takizawa, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 324 days.

(21) Appl. No.: 15/429,916

(22) Filed: Feb. 10, 2017

(65) Prior Publication Data
US 2017/0150874 A1    Jun. 1, 2017

Related U.S. Application Data

(63) Continuation of application No. PCT/JP2015/079865, filed on Oct. 22, 2015.

(30) Foreign Application Priority Data

Mar. 30, 2015   (JP) ................. 2015-070163

(51) Int. Cl.
*A61B 1/04*     (2006.01)
*A61B 1/00*     (2006.01)
(Continued)

(52) U.S. Cl.
CPC .......... *A61B 1/041* (2013.01); *A61B 1/00009* (2013.01); *A61B 1/00039* (2013.01); (Continued)

(58) Field of Classification Search
CPC . A61B 1/041; A61B 1/00009; A61B 1/00039; A61B 1/00158; A61B 1/00174; A61B 1/0684; A61B 5/073
See application file for complete search history.

(56) References Cited

U.S. PATENT DOCUMENTS 8,162,821 B2    4/2012   Kawano et al.
9,039,606 B2 *  5/2015   Uchiyama .......... A61B 1/00158
                                                 600/114
(Continued)

FOREIGN PATENT DOCUMENTS

JP    2007-175447 A    7/2007
WO    WO 2007/077922 A1  7/2007
(Continued)

OTHER PUBLICATIONS

International Search Report dated Jan. 19, 2016 issued in PCT/JP2015/079865.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A capsule endoscope system includes: a capsule endoscope configured to be introduced into a subject and having a magnetic field response unit configured to respond to a magnetic field and having an imaging unit configured to image an object; a magnetic field generating unit configured to generate the magnetic field to guide the capsule endoscope; an input unit configured to input commands for changing at least one of a position and a posture of the capsule endoscope; a setting unit configured to set a reference distance between the imaging unit and the object; a detection unit configured to detect a distance between the object and the imaging unit; and a magnetic field controller configured to control the magnetic field generating unit to generate the magnetic field based on the distance and the commands while a difference between the distance and the reference distance is maintained within a certain range.

13 Claims, 27 Drawing Sheets

(51) Int. Cl.
*A61B 1/06* (2006.01)
*A61B 5/07* (2006.01)

(52) U.S. Cl.
CPC ...... *A61B 1/00158* (2013.01); *A61B 1/00174* (2013.01); *A61B 1/0684* (2013.01); *A61B 5/073* (2013.01); *G06T 2207/10068* (2013.01)

(56) References Cited

U.S. PATENT DOCUMENTS

| | | | |
|---|---|---|---|
| 9,208,564 B2 * | 12/2015 | Degenhardt | A61B 1/00158 |
| 2007/0161885 A1 * | 7/2007 | Kimchy | A61B 5/073 600/407 |
| 2007/0255087 A1 * | 11/2007 | Minai | A61B 1/041 600/12 |
| 2008/0300453 A1 | 12/2008 | Aoki et al. | |
| 2009/0253954 A1 * | 10/2009 | Katayama | A61B 1/041 600/103 |
| 2010/0067808 A1 * | 3/2010 | Matsuzaki | A61B 1/041 382/218 |
| 2010/0149183 A1 * | 6/2010 | Loewke | G06K 9/00134 345/424 |
| 2010/0268026 A1 | 10/2010 | Takizawa | |
| 2010/0272318 A1 * | 10/2010 | Cabiri | A61B 1/00096 382/106 |
| 2010/0312077 A1 * | 12/2010 | Takahashi | A61B 1/041 600/302 |
| 2012/0095289 A1 | 4/2012 | Kawano et al. | |
| 2012/0095290 A1 | 4/2012 | Kawano | |
| 2012/0116162 A1 | 5/2012 | Kawano et al. | |
| 2013/0278738 A1 * | 10/2013 | Hayashi | H04N 5/2354 348/68 |
| 2014/0046131 A1 * | 2/2014 | Morita | A61B 1/00179 600/109 |

FOREIGN PATENT DOCUMENTS

| | | |
|---|---|---|
| WO | WO 2010/047357 A1 | 4/2010 |
| WO | WO 2011/058800 A1 | 5/2011 |
| WO | WO 2011/061977 A1 | 5/2011 |
| WO | WO 2011/118253 A1 | 9/2011 |

* cited by examiner

CAPSULE ENDOSCOPE SYSTEM AND MAGNETIC FIELD GENERATING DEVICE

CROSS-REFERENCE TO RELATED APPLICATION

This application is a continuation of PCT International Application No. PCT/JP2015/079865 filed on Oct. 22, 2015 which claims the benefit of priority from Japanese Patent Application No. 2015-070163 filed on Mar. 30, 2015, the entire contents of which are incorporated herein by reference.

BACKGROUND

1. Technical Field

The disclosure relates to a capsule endoscope system and a magnetic field generating device for magnetically guiding a capsule endoscope which is introduced into a subject and moves inside the subject to acquire in-vivo information of the subject.

2. Related Art

Conventionally, a technique that magnetically guides a capsule endoscope introduced into a subject such as a patient is known (see WO 2007/077922 A). In this technique, a user such as a doctor observes a desired region by controlling each of an observation direction and a propulsive direction of the capsule endoscope using an operating device such as a joystick while viewing a display unit that displays an in-vivo image transmitted from the capsule endoscope.

SUMMARY

In some embodiments, a capsule endoscope system includes: a capsule endoscope configured to be introduced into a subject and having a magnetic field response unit configured to respond to a magnetic field applied from outside and having an imaging unit configured to image an object to generate an image of the object; a magnetic field generating unit configured to generate the magnetic field to guide the capsule endoscope; an input unit configured to input commands for changing at least one of a position and a posture of the capsule endoscope; a setting unit configured to set a reference distance between the imaging unit and the object; a detection unit configured to detect a distance between the object and the imaging unit; and a magnetic field controller configured to control the magnetic field generating unit to generate the magnetic field based on the distance and the commands so as to guide the capsule endoscope while a difference between the distance and the reference distance is maintained within a certain range.

In some embodiments, a magnetic field generating device is configured to guide a capsule endoscope. The capsule endoscope is configured to be introduced into a subject and has a magnetic field response unit configured to respond to a magnetic field applied from outside and has an imaging unit configured to image an object to generate an image of the object. The magnetic field generating device includes: a magnetic field generating unit configured to generate the magnetic field to guide the capsule endoscope; an input unit configured to input commands for changing at least one of a position and a posture of the capsule endoscope; a setting unit configured to set a reference distance between the imaging unit and the object; a detection unit configured to detect a distance between the object and the imaging unit; and a magnetic field controller configured to control the magnetic field generating unit to generate the magnetic field based on the distance and the commands so as to guide the capsule endoscope while a difference between the distance and the reference distance is maintained within a certain range.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, a capsule endoscope system which is an embodiment according to the present invention will be described by using an example of a capsule endoscope guidance system that uses a capsule endoscope which is orally introduced into a subject and drifts in a liquid stored in a stomach of the subject. However, the capsule endoscope system is not limited to this, and it is possible to use various capsule endoscopes such as, for example, a capsule endoscope configured to move in a lumen from the esophagus to the anus of the subject and a capsule endoscope configured to be introduced from the anus along with an isotonic fluid. The invention is not limited by the embodiment. The same reference signs are used to designate the same elements throughout the drawings.

First Embodiment

Configuration of Capsule Endoscope System

Figure 1:
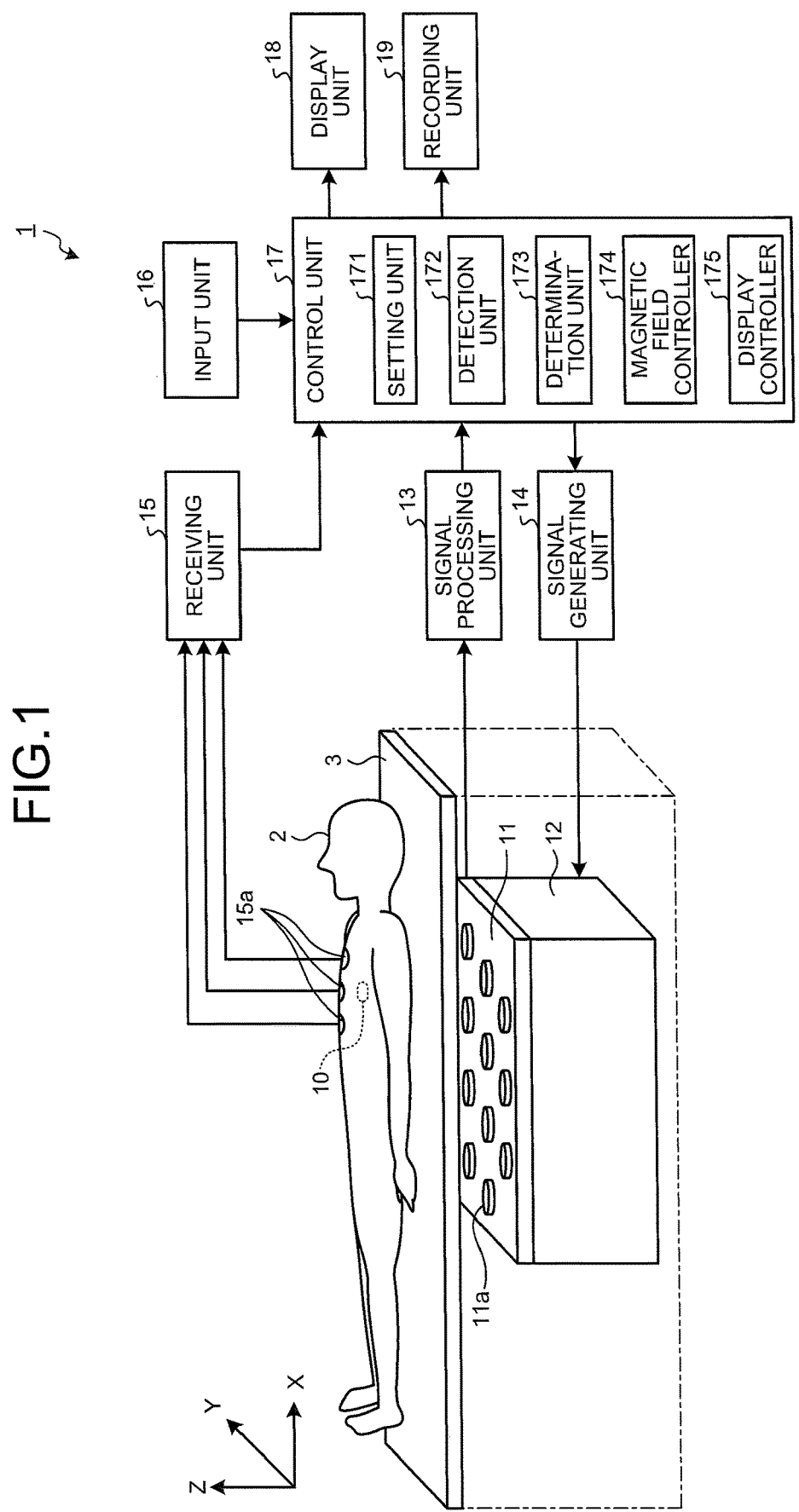
FIG. 1 is a diagram illustrating a configuration example of a capsule endoscope system according to a first embodiment of the present invention.

FIG. 1 is a diagram illustrating a configuration example of a capsule endoscope system according to a first embodiment of the present invention. A capsule endoscope system 1 illustrated in FIG. 1 includes a capsule endoscope 10 which is configured to be introduced into a subject 2 and wirelessly transmits an image signal (image information) that has been acquired by capturing an image inside the subject 2 to the outside of the subject 2, a position detection unit 11 that detects a position of the capsule endoscope 10 through a plurality of sensing coils 11a provided below a bed 3 on which the subject 2 is laid, a magnetic field generating unit 12 that generates a magnetic field to magnetically guide the capsule endoscope 10, a signal processing unit 13 that processes a signal outputted from the position detection unit 11, a signal generating unit 14 that generates a signal to operate the magnetic field generating unit 12, a receiving unit 15 that receives the image signal wirelessly transmitted from the capsule endoscope 10, an input unit 16 for performing a guiding operation of the capsule endoscope 10, a control unit 17 that performs processing to display an image inside the subject 2 (hereinafter referred to as an "in-vivo image") based on the image signal received by the receiving unit 15, a display unit 18 that displays the in-vivo image and other information, and a recording unit 19 that records image information captured by the capsule endoscope 10 and the like. The bed 3 is arranged so that un upper surface of the bed 3 (a surface on which the subject 2 is laid) is in parallel with a horizontal surface (a surface perpendicular to a direction of gravitational force). Hereinafter, a longitudinal direction of the bed 3 is defined as an X direction, a direction of a shorter side of the bed 3 is defined as a Y direction, and a vertical direction (the direction of gravitational force) is defined as a Z direction. In the first embodiment, the magnetic field generating unit 12, the input unit 16, and the control unit 17 function as a magnetic field generating device.

Figure 2:
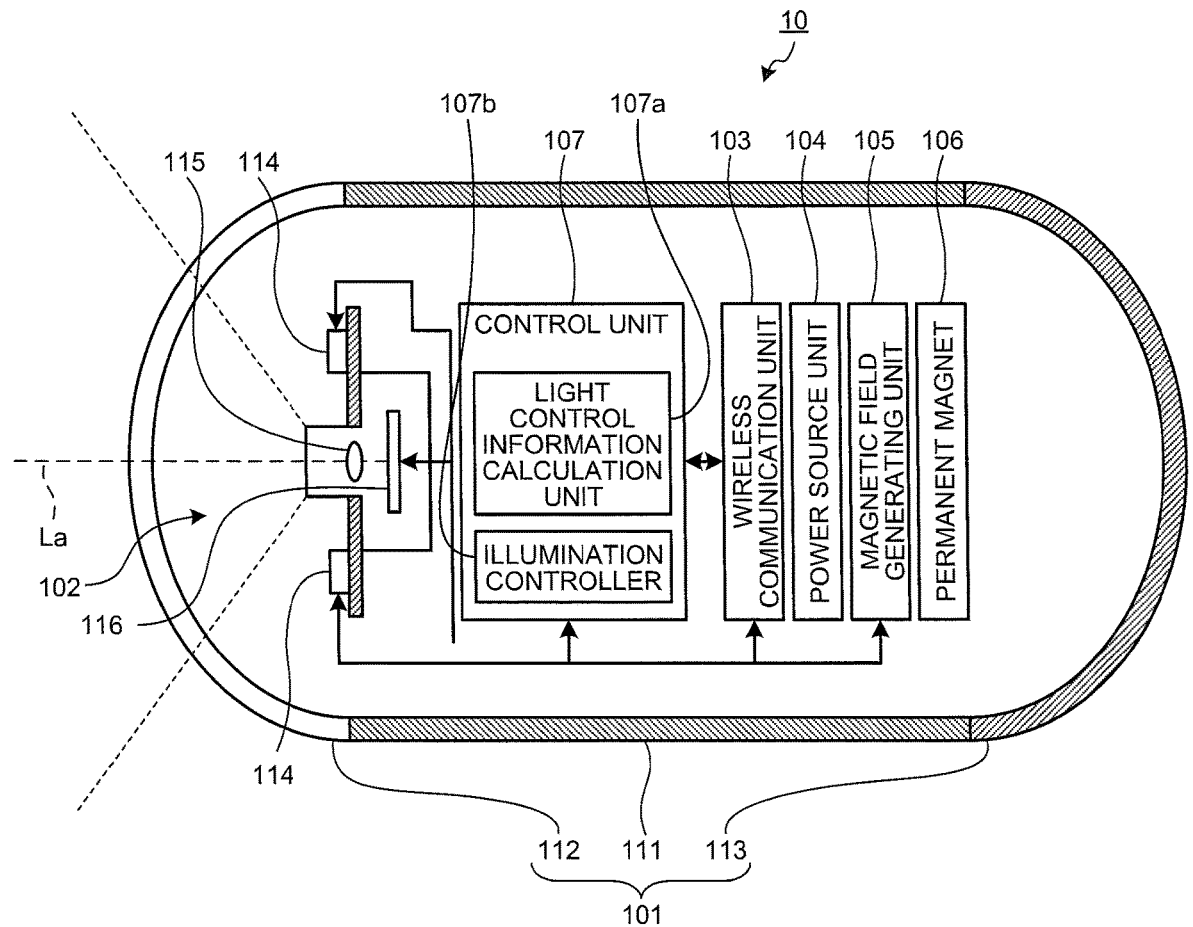
FIG. 2 is a schematic diagram illustrating an example of an internal structure of a capsule endoscope according to the first embodiment of the present invention.

The capsule endoscope 10 is introduced into an organ of the subject 2 along with a predetermined liquid by oral ingestion or the like. Thereafter the capsule endoscope 10 moves inside a digestive canal and is finally discharged to the outside of the subject 2. The capsule endoscope 10 sequentially captures in-vivo images of the subject 2 and sequentially and wirelessly transmits the obtained in-vivo images to the external receiving unit 15. Here, a configuration of the capsule endoscope 10 will be described. FIG. 2 is a schematic diagram illustrating an example of an internal structure of the capsule endoscope 10.

The capsule endoscope 10 illustrated in FIG. 2 includes a capsule-shaped casing 101 which is an outer package large enough to be easily introduced into an organ of the subject 2, an imaging unit 102 that images the subject 2 to generate an image signal, a wireless communication unit 103 that wirelessly transmits the image signal generated by the imaging unit 102 to the outside, a power source unit 104 that supplies power to each element of the capsule endoscope 10, a magnetic field generating unit 105 that generates an alternating magnetic field for detecting a position of the capsule endoscope 10, a permanent magnet 106 that enables magnetic guidance performed by the magnetic field generating unit 12, and a control unit 107 that controls each element of the capsule endoscope 10.

The capsule-shaped casing 101 is an outer case large enough to be introduced into an organ of the subject 2. The capsule-shaped casing 101 is realized by closing open ends of both sides of a tubular casing 111 with dome-shaped casings 112 and 113. The dome-shaped casing 112 is a dome-shaped optical member that is transparent to light at a predetermined wavelength band such as visible light. The tubular casing 111 and the dome-shaped casing 113 are colored casings that are substantially opaque to visible light.

As illustrated in FIG. 2, the capsule-shaped casing 101 formed by the tubular casing 111 and the dome-shaped casings 112 and 113 internally includes the imaging unit 102, the wireless communication unit 103, the power source unit 104, the magnetic field generating unit 105, the permanent magnet 106, and control unit 107 in a liquid-tight manner.

The imaging unit 102 has an illumination unit 114 such as an LED (Light Emitting Diode), an optical system 115 such as a condenser lens, and an image sensor 116 such as CMOS (Complementary Metal Oxide Semiconductor) or CCD (Charge Coupled Device). The illumination unit 114 emits illumination light, such as white light, to an imaging visual field of the image sensor 116 and illuminates the subject 2 in the imaging visual field through the dome-shaped casing 112 under control of the control unit 107. The optical system 115 collects reflection light from the imaging visual field on an imaging surface of the image sensor 116 and forms a subject image. The optical system 115 is formed by using at least one lens. The image sensor 116 receives the reflection light from the imaging visual field that has been collected on the imaging surface, and performs photoelectric conversion on a received optical signal to generate an image signal indicating the subject image in the imaging visual field, that is, an in-vivo image of the subject 2.

In this embodiment, only one imaging unit 102 is provided in the capsule endoscope 10. However, the imaging unit 102 may also be provided in the dome-shaped casing 113 so that forward and backward images can be captured with respect to an axis La of the capsule endoscope 10. In this case, the dome-shaped casing 113 is also formed of a dome-shaped optical member that is transparent to light at a predetermined wavelength band such as visible light. Further, in this case, the two imaging units 102 are arranged so that an optical axis of each imaging unit 102 is substantially in parallel with or substantially coincident with the axis La, which is a central axis in the longitudinal direction of the capsule-shaped casing 101, and each imaging visual field faces the opposite direction.

The wireless communication unit 103 sequentially and wirelessly transmits image signals generated by the imaging unit 102 to the outside through an antenna not illustrated in the drawings. Specifically, the wireless communication unit 103 acquires an image signal generated by the imaging unit 102 from the control unit 107 and generates a wireless signal by performing signal processing such as modulation on the image signal. The wireless communication unit 103 transmits the wireless signal to the receiving unit 15 provided outside the subject 2.

The power source unit 104 is a power storage unit such as a button-type battery or a capacitor and has a magnetic switch, an optical switch, or a switch unit (not illustrated in the drawings) that is turned on or off by a command from the control unit 107. The power source unit 104 receives a high-frequency signal of a specific pattern, which is a command that turns on or off the switch unit and which is applied from outside through the wireless communication unit 103, and switches between ON and OFF states of a power supply by control of the control unit 107 based on the high-frequency signal. When the power supply is in an ON state, the power source unit 104 supplies power of the power storage unit to each unit of the capsule endoscope 10. When the power supply is in an OFF state, the power source unit 104 stops power supply to each unit of the capsule endoscope 10.

The magnetic field generating unit 105 includes a transmitting coil that forms a part of a resonance circuit and generates a magnetic field while a current is flowing and a capacitor that forms the resonance circuit along with the transmitting coil. The magnetic field generating unit 105 receives power supply from the power source unit 104 and generates an alternating magnetic field of a predetermined frequency. In the first embodiment, the magnetic field generating unit 105 functions as a magnetic field response unit that responds to a magnetic field applied from the outside.

The permanent magnet 106 is arranged to be fixed inside the capsule-shaped casing 101 so that a magnetization direction has an inclination with respect to the axis La. In the first embodiment, the permanent magnet 106 is arranged so that the magnetization direction is perpendicular to the axis La. The permanent magnet 106 operates following a magnetic field applied from the outside. Aa a result, magnetic guidance of the capsule endoscope 10 by the magnetic field generating unit 12 described later is realized.

The control unit 107 is formed by using a CPU (Central Processing Unit) and the like. The control unit 107 controls each operation of the imaging unit 102 and the wireless communication unit 103 and further controls input/output of signals between these elements. Specifically, every time the image sensor 116 generates an image signal, the control unit 107 acquires the image signal and performs predetermined processing on the image signal and further controls the wireless communication unit 103 to sequentially and wirelessly transmit the image signal to the outside along the time series. The control unit 107 has a light control information calculation unit 107a and an illumination controller 107b.

The light control information calculation unit 107a calculates light control information related to a light emission amount and an exposure time of the illumination unit 114 based on the image signal generated by the image sensor 116. Specifically, the light control information calculation unit 107a calculates a light emission amount and an exposure time of light emitted from the illumination unit 114 based on the brightness of an in-vivo image corresponding to the image signal generated by the image sensor 116.

The illumination controller 107b controls the illumination unit 114 based on the light control information calculated by the light control information calculation unit 107a. Specifically, the illumination controller 107b causes the illumination unit 114 to emit illumination light based on the light emission amount and the exposure time calculated by the light control information calculation unit 107a.

With reference to FIG. 1 again, the capsule endoscope system 1 will be continuously described.

The position detection unit 11 detects a position of the capsule endoscope 10 in the subject 2 through the plurality of sensing coils 11a provided below the bed 3 on which the subject 2 is laid. Specifically, the position detection unit 11 detects the position of the capsule endoscope 10 in the subject 2 by capturing, by using the plurality of sensing coils 11a, the alternating magnetic field generated by the magnetic field generating unit 105 of the capsule endoscope 10.

The magnetic field generating unit 12 magnetically guides the capsule endoscope 10 in the subject 2. The magnetic field generating unit 12 is realized by using, for example, a plurality of coils and generates a guiding magnetic field by using power supplied from a power supply unit not illustrated in the drawings. The magnetic field generating unit 12 applies the guiding magnetic field to the permanent magnet 106 of the capsule endoscope 10 and magnetically captures the capsule endoscope 10 by an action of the guiding magnetic field. The magnetic field generating unit 12 controls a three-dimensional posture of the capsule endoscope 10 in the subject 2 by changing a magnetic field direction of the guiding magnetic field applied to the capsule endoscope 10 in the subject 2. Specifically, the magnetic field generating unit 12 controls the posture of the capsule endoscope 10, a distance to the subject 2, and an imaging direction of the capsule endoscope 10 by changing the magnetic field direction of the guiding magnetic field applied to the capsule endoscope 10 in the subject 2. The magnetic field generating unit 12 may be realized by using a permanent magnet instead of a plurality of coils.

The signal processing unit 13 outputs a signal obtained by performing predetermined processing on a result of detection completed by the position detection unit 11 to the control unit 17. Specifically, the signal processing unit 13 performs, for example, demodulation processing on an analog signal detected by the position detection unit 11 and thereafter performs A/D conversion processing on the analog signal. Then the signal processing unit 13 outputs the A/D-converted signal to the control unit 17.

The signal generating unit 14 generates a signal to cause the magnetic field generating unit 12 to operate and outputs the signal to the magnetic field generating unit 12 under control of the control unit 17.

The receiving unit 15 includes a plurality of receiving antennas 15a and receives an image signal which includes spatial information around the capsule endoscope 10 and which is wirelessly transmitted from the capsule endoscope 10 through the plurality of receiving antennas 15a. The receiving unit 15 performs demodulation processing, A/D conversion processing, and the like on the image signal received from the capsule endoscope 10 and then outputs the image signal to the control unit 17.

Figure 3:
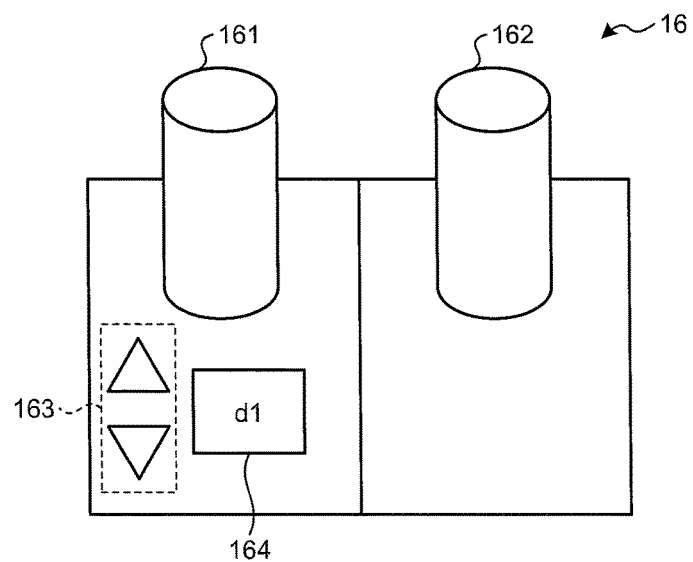
FIG. 3 is a schematic configuration diagram of an input unit according to the first embodiment of the present invention.

The input unit 16 receives various kinds of information according to an input operation performed by a user such as a doctor and outputs the received various information to the control unit 17. FIG. 3 is a schematic configuration diagram of the input unit 16. The input unit 16 illustrated in FIG. 3 is realized by using input devices such as joysticks, a button, and a switch. The input unit 16 receives various information according to an input operation performed by a user such as a doctor. The input unit 16 has a joystick 161 that receives an input of a command signal that instructs a posture of the capsule endoscope 10, a joystick 162 that receives an input of a command signal that instructs a movement (position) of the capsule endoscope 10, a distance input unit 163 that receives an input of a command signal that sets a distance between the capsule endoscope 10 and the subject 2, and a display unit 164 that displays the distance between the capsule endoscope 10 and the subject 2, an input of which has been received by the distance input unit 163. The input unit 16 may be realized by using input devices such as a keyboard, a mouse, and a touch panel.

With reference to FIG. 1 again, the capsule endoscope system 1 will be continuously described.

The control unit 17 is formed by using a CPU (Central Processing Unit) and perform overall control of each element of the capsule endoscope system 1. The control unit 17 has a setting unit 171, a detection unit 172, a determination unit 173, a magnetic field controller 174, and a display controller 175.

The setting unit 171 sets a reference distance between the imaging unit 102 (the capsule endoscope 10) and the subject 2. Specifically, the setting unit 171 sets the reference distance between the imaging unit 102 and the subject 2 based on the command signal inputted from the input unit 16.

The detection unit 172 detects a spatial relationship between an object (a wall surface of the subject 2) and a periphery of the capsule endoscope 10. Specifically, the detection unit 172 detects a distance from the image sensor 116 to the subject 2 as a spatial relationship based on the brightness of an image corresponding to image data generated by the image sensor 116.

The determination unit 173 determines whether or not the distance calculated by the detection unit 172 is smaller than the reference distance set by the setting unit 171.

The magnetic field controller 174 controls a guiding magnetic field that is applied to the permanent magnet 106 of the capsule endoscope 10 by the magnetic field generating unit 12 so as to guide the capsule endoscope 10 while maintaining a spatial relationship between the capsule endoscope 10 and a periphery of the capsule endoscope 10, based on a result of detection completed by the detection unit 172 and command signal received by the input unit 16.

The display controller 175 controls a display mode of the display unit 18. Specifically, the display controller 175 superimposes various information on an in-vivo image displayed on the display unit 18 and causes the display unit 18 to display the in-vivo image on which the various information is superimposed. Further, the display controller 175 causes the display unit 18 to display various information related to the capsule endoscope system 1.

The display unit 18 is realized by using a display panel such as a liquid crystal panel or an organic EL (Electro Luminescence) panel and displays various information which is instructed to be displayed on the control unit 17. Specifically, the display unit 18 displays an in-vivo image group of the subject 2, which is captured by the capsule endoscope 10 under control of the display controller 175.

The recording unit 19 records in-vivo images captured by the capsule endoscope 10 and various information that is being processed by a program executed by the capsule endoscope system 1. The recording unit 19 is realized by using, for example, a recording medium rewritably storing information, such as a flash memory or a hard disk.

In the capsule endoscope system 1 configured as described above, after the capsule endoscope 10 and a predetermined liquid are orally ingested into the subject 2, a user operates the input unit 16 while viewing an in-vivo image displayed on the display unit 18 and performs observation and the like of the subject 2 while moving an observation position of the capsule endoscope 10 by the magnetic field generated by the magnetic field generating unit 12.

Processing of Capsule Endoscope System

Figure 4:
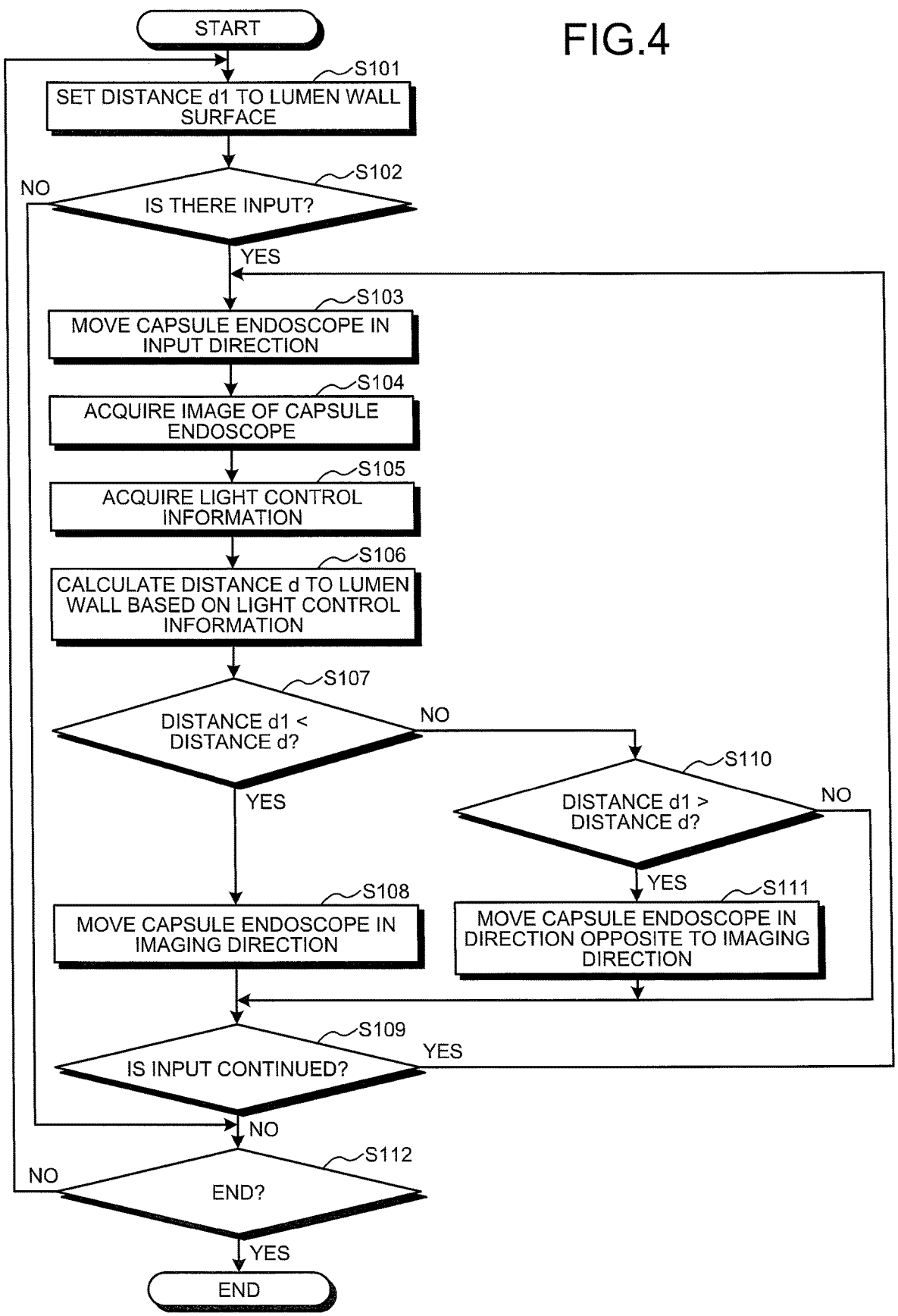
FIG. 4 is a flowchart illustrating an overview of processing performed by the capsule endoscope system according to the first embodiment of the present invention.

Next, processing performed by the capsule endoscope system 1 will be described. FIG. 4 is a flowchart illustrating an overview of the processing performed by the capsule endoscope system 1. Hereinafter, a case in which the stomach of the subject 2 is observed by using the capsule endoscope 10 will be described.

As illustrated in FIG. 4, first, the setting unit 171 sets a reference distance d1 from the capsule endoscope 10 to a lumen wall surface of the subject 2 based on the command signal inputted from the distance input unit 163 (step S101).

Subsequently, when there is an input of the command signal, which instructs a movement of the capsule endoscope 10 in a direction perpendicular to an imaging direction, from the joystick 162 (step S102: Yes), the magnetic field controller 174 causes the magnetic field generating unit 12 to generate a magnetic field by controlling the signal generating unit 14 and moves the capsule endoscope 10 in an input direction (step S103).

Subsequently, the control unit 17 acquires, through the receiving unit 15, an image generated by the capsule endoscope 10 (step S104) and acquires light control information included in the image (step S105).

Thereafter, the detection unit 172 calculates a distance d from the capsule endoscope 10 to a lumen wall of the subject 2 based on the light control information included in the image generated by the capsule endoscope 10, acquired through the receiving unit 15 (step S106).

Figure 5:
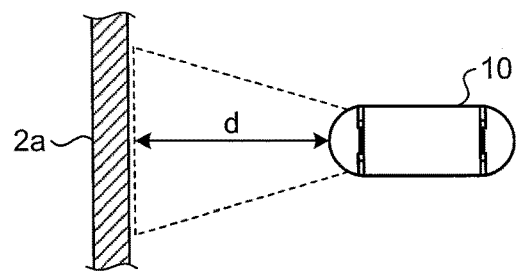
FIG. 5 is a diagram for schematically describing a calculation method of a distance calculated by a detection unit according to the first embodiment of the present invention.

FIG. 5 is a diagram for schematically describing a calculation method of a distance calculated by the detection unit 172. As illustrated in FIG. 5, the detection unit 172 detects the distance d from the capsule endoscope 10 to a wall surface 2a of the subject 2 based on the amount of light emitted from the illumination unit 114 when appropriate brightness (appropriate exposure) is obtained according to the light control information calculated by the light control information calculation unit 107a of the capsule endoscope 10. The detection unit 172 calculates the distance d so that the amount of light emitted from the illumination unit 114 is greater as the distance d from the capsule endoscope 10 to the wall surface 2a of the subject 2 becomes greater. In the case of FIG. 5, in the capsule endoscope 10, after the illumination unit 114 emits light under control of the illumination controller 107b, the light control information calculation unit 107a calculates the brightness of image based on image data generated by the image sensor 116, and the illumination controller 107b controls the amount of light emitted from the illumination unit 114 based on the brightness of image calculated by the light control information calculation unit 107a and causes the illumination unit 114 to emit light.

Figure 6A:
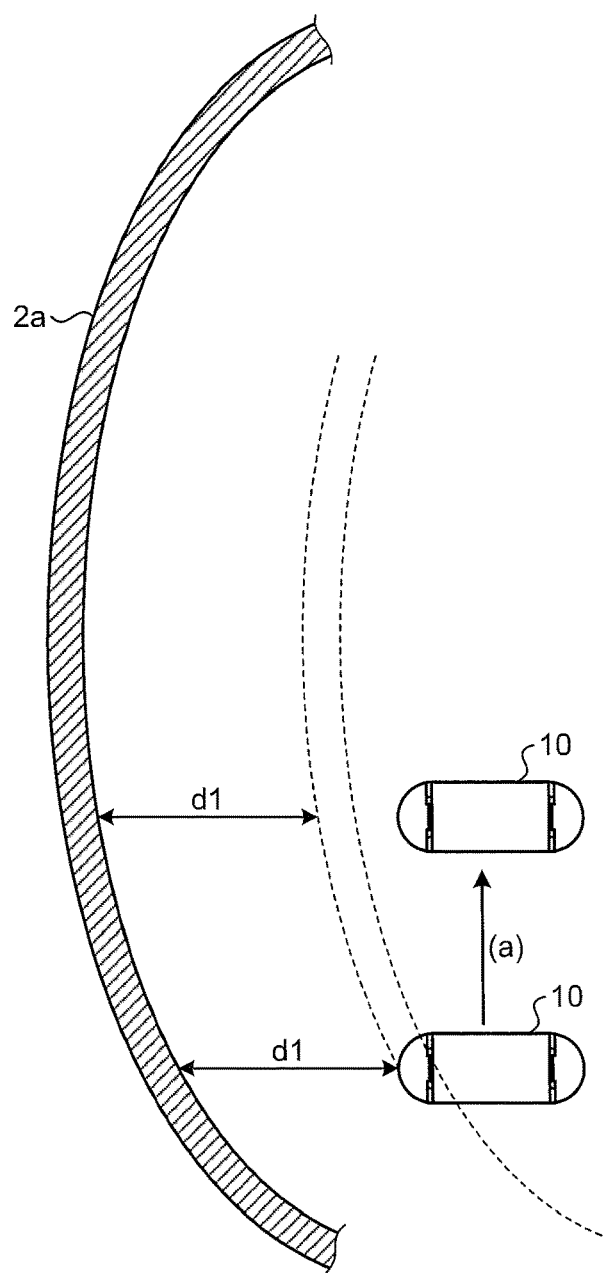
FIG. 6A is a diagram schematically illustrating a transition in a subject of the capsule endoscope according to the first embodiment of the present invention.

Subsequently, the determination unit 173 determines whether or not the distance d calculated by the detection unit 172 is greater than the reference distance d1 set by the setting unit 171 (step S107). Specifically, as illustrated in FIG. 6A, after the capsule endoscope 10 moves in a direction of the arrow (a), the determination unit 173 determines that the distance d from the capsule endoscope 10 to the wall surface 2a of the subject 2 is greater than the reference distance d1 set by the setting unit 171. When the determination unit 173 determines that the distance d calculated by the detection unit 172 is greater than the reference distance d1 set by the setting unit 171 (step S107: Yes), the control unit 17 proceeds to step S108 described below. On the other hand, when the determination unit 173 determines that the distance d calculated by the detection unit 172 is not greater than the reference distance d1 set by the setting unit 171 (step S107: No), the control unit 17 proceeds to step S110 described below.

Figure 6B:
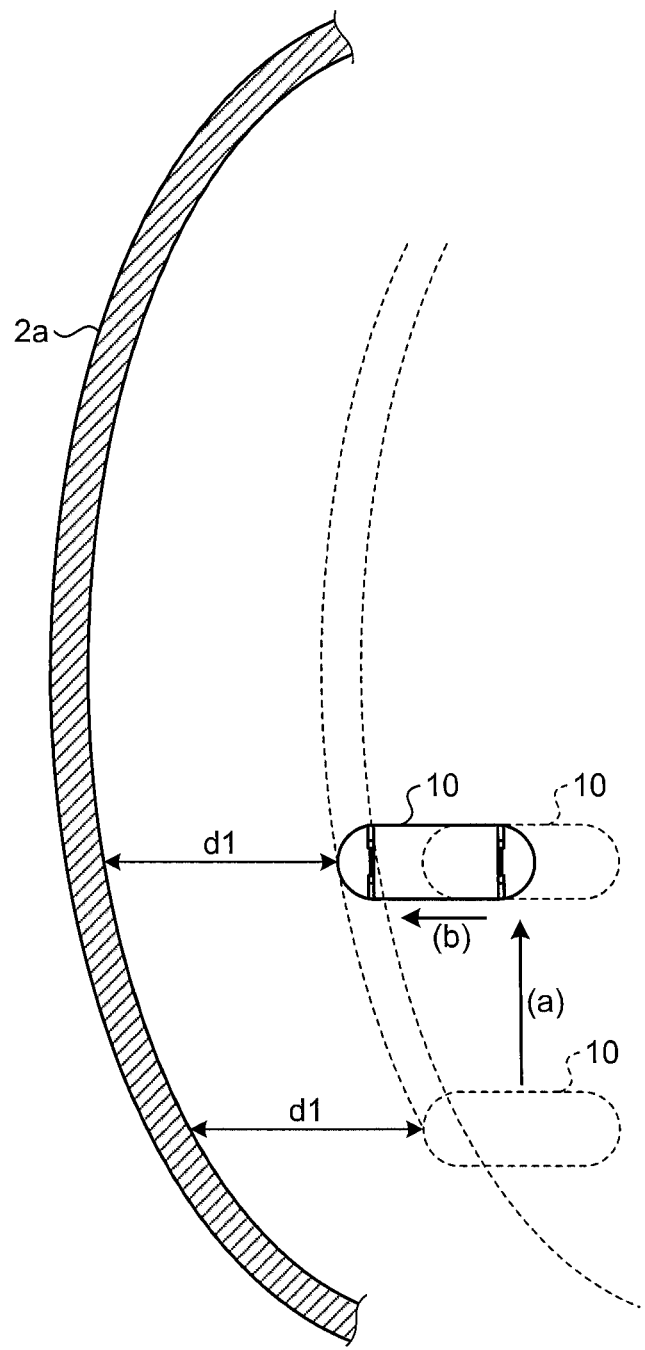
FIG. 6B is a diagram schematically illustrating a transition in the subject of the capsule endoscope according to the first embodiment of the present invention.

In step S108, the magnetic field controller 174 controls the guiding magnetic field generated by the magnetic field generating unit 12 through the signal generating unit 14 so that the capsule endoscope 10 moves in the imaging direction according to the command signal from the joystick 162 to instruct a movement of the capsule endoscope 10. Specifically, as illustrated in FIG. 6B, the magnetic field controller 174 controls the guiding magnetic field generated by the magnetic field generating unit 12 through the signal generating unit 14 so that the capsule endoscope 10 moves in the imaging direction so that the capsule endoscope 10 moves in a direction of the arrow (b).

Figure 6C:
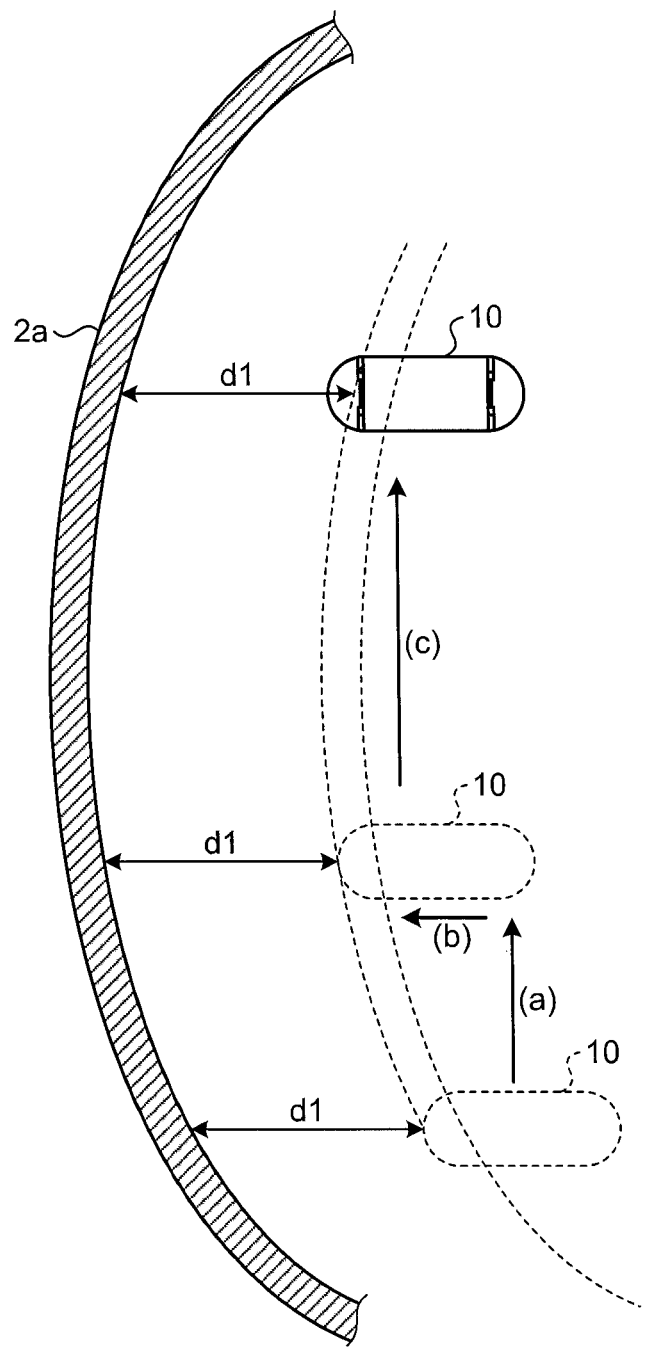
FIG. 6C is a diagram schematically illustrating a transition in the subject of the capsule endoscope according to the first embodiment of the present invention.

Subsequently, if the input of the command signal from the joystick 162 to instruct a movement of the capsule endoscope 10 is continued (step S109: Yes), the control unit 17 returns to step S103. In this case, as illustrated in FIGS. 6B and 6C, the magnetic field controller 174 controls the guiding magnetic field generated by the magnetic field generating unit 12 through the signal generating unit 14 so that the capsule endoscope 10 moves in the imaging direction so that the capsule endoscope 10 moves in a direction of the arrow (c) (a direction perpendicular to the imaging direction). On the other hand, if the input of the command signal from the joystick 162 to instruct a movement of the capsule endoscope 10 is not continued (step S109: No), the control unit 17 proceeds to step S112 described below.

In step S110, the determination unit 173 determines whether or not the distance d calculated by the detection unit 172 is smaller than the reference distance d1 set by the setting unit 171. Specifically, as illustrated in FIG. 6C, after the capsule endoscope 10 moves in a direction of the arrow (c), the determination unit 173 determines whether or not the distance d from the capsule endoscope 10 to the wall surface 2a of the subject 2 is smaller than the reference distance d1 set by the setting unit 171. When the determination unit 173 determines that the distance d calculated by the detection unit 172 is smaller than the reference distance d1 set by the setting unit 171 (step S110: Yes), the control unit 17 proceeds to step S111 described below. On the other hand, when the determination unit 173 determines that the distance d calculated by the detection unit 172 is not smaller than the reference distance d1 set by the setting unit 171 (step S110: No), the control unit 17 proceeds to step S109.

Figure 6D:
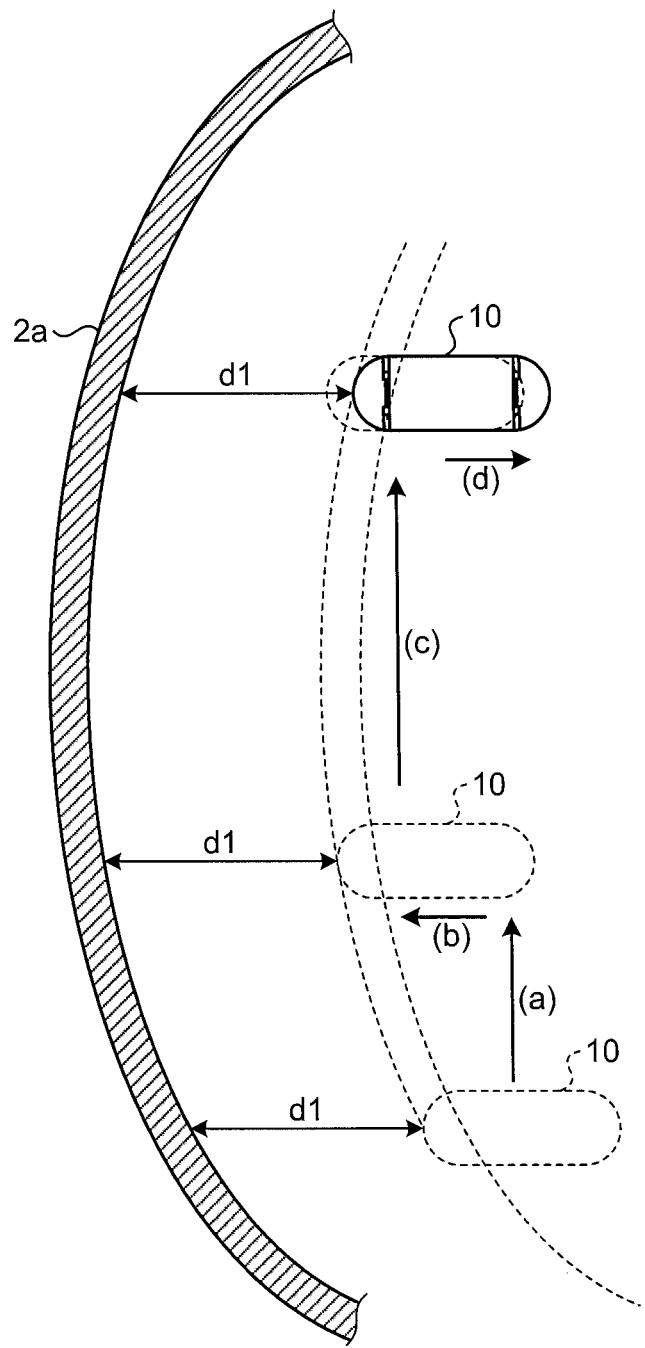
FIG. 6D is a diagram schematically illustrating a transition in the subject of the capsule endoscope according to the first embodiment of the present invention.

In step S111, the magnetic field controller 174 controls the guiding magnetic field generated by the magnetic field generating unit 12 through the signal generating unit 14 so that the capsule endoscope 10 moves in a direction opposite to the imaging direction. Specifically, as illustrated in FIG. 6D, the magnetic field controller 174 controls the guiding magnetic field generated by the magnetic field generating unit 12 through the signal generating unit 14 so that the capsule endoscope 10 moves in a direction of the arrow (d). After step S111, the control unit 17 proceeds to step S109.

In step S102, if there is no input of command signal from the joystick 162 to instruct a movement of the capsule endoscope 10 (step S102: No), the control unit 17 proceeds to step S112.

Subsequently, when ending the observation of the subject 2 performed by using the capsule endoscope 10 (step S112: Yes), the control unit 17 ends the present processing. On the other hand, when not ending the observation of the subject 2 performed by using the capsule endoscope 10 (step S112: No), the control unit 17 returns to step S101.

According to the first embodiment, the magnetic field controller 174 automatically moves the position of the capsule endoscope 10 so as to maintain the distance set by the setting unit 171 based on the distance calculated by the detection unit 172 and the reference distance set by the setting unit 171. Consequently, the guiding operation of the capsule endoscope 10 is increased, and therefore, it is possible to facilitate the observation of the subject 2.

Further, according to the first embodiment, the magnetic field controller 174 guides the capsule endoscope 10 so that a difference between the distance calculated by the detection unit 172 and the reference distance set by the setting unit 171 is maintained within a certain range. Therefore, it is possible to guide the capsule endoscope 10 to a desired position without causing a user to be conscious of the guiding operation in the observation direction and the vertical direction of the capsule endoscope 10. As a result, it is possible to facilitate the operation and improve the operability.

Further, according to the first embodiment, since the distance between the capsule endoscope 10 and the wall surface 2a of the subject 2 is detected by using only an illumination function and an imaging function which are originally included in the capsule endoscope 10, it is not necessary to add a new configuration to the capsule endoscope 10. Therefore, it is possible to easily assemble the capsule endoscope 10 and manufacture the capsule endoscope 10 at a low cost.

First Modified Example of First Embodiment

Next, a first modified example of the first embodiment of the present invention will be described. The first modified example of the first embodiment has the same configuration as that of the capsule endoscope system 1 according to the first embodiment to change a posture (rotation) of the capsule endoscope and move the capsule endoscope in accordance with the observation direction and the vertical direction. An operation according to the first modified example of the first embodiment will be described below. The same elements as those of the capsule endoscope system 1 according to the first embodiment are denoted by the same reference signs, and the explanation thereof will not be repeated.

FIGS. 7A to 7G are diagrams schematically illustrating a transition in the subject 2 of the capsule endoscope 10 according to the first modified example of the first embodiment.

Figure 7A:
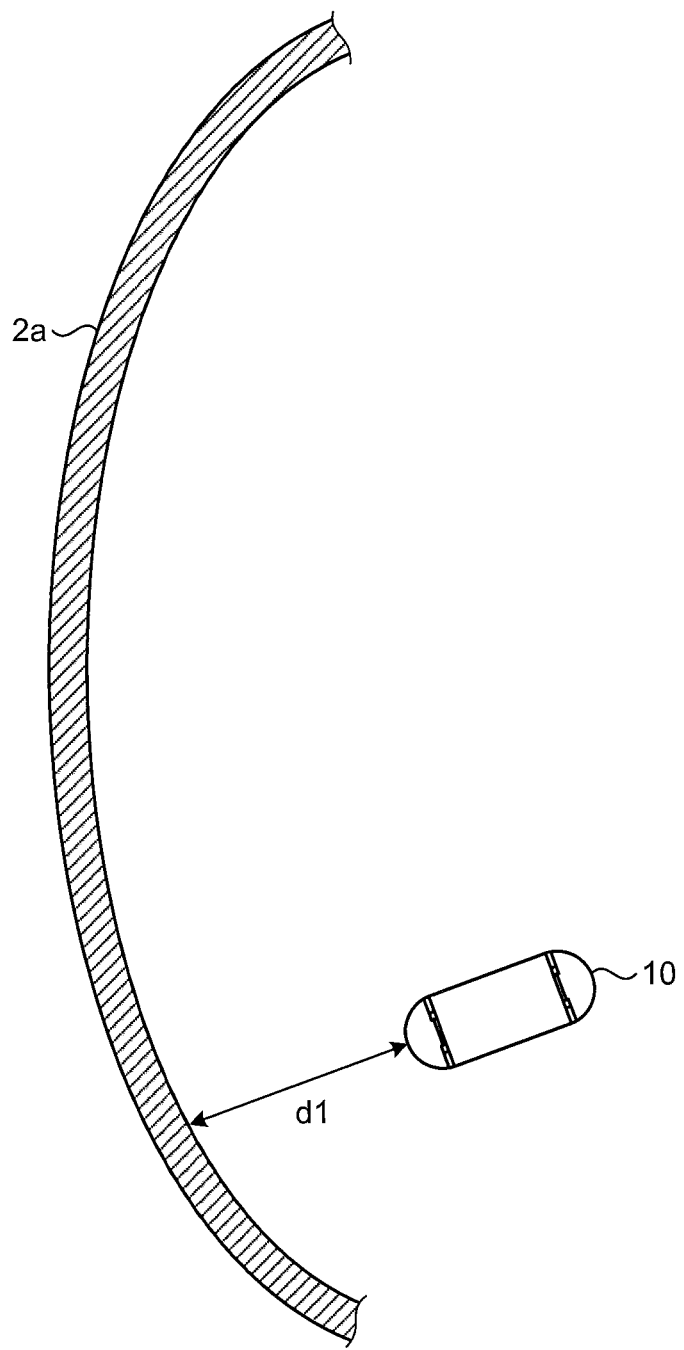
FIG. 7A is a diagram schematically illustrating a transition in a subject of a capsule endoscope according to a first modified example of the first embodiment of the present invention.
Figure 7B:
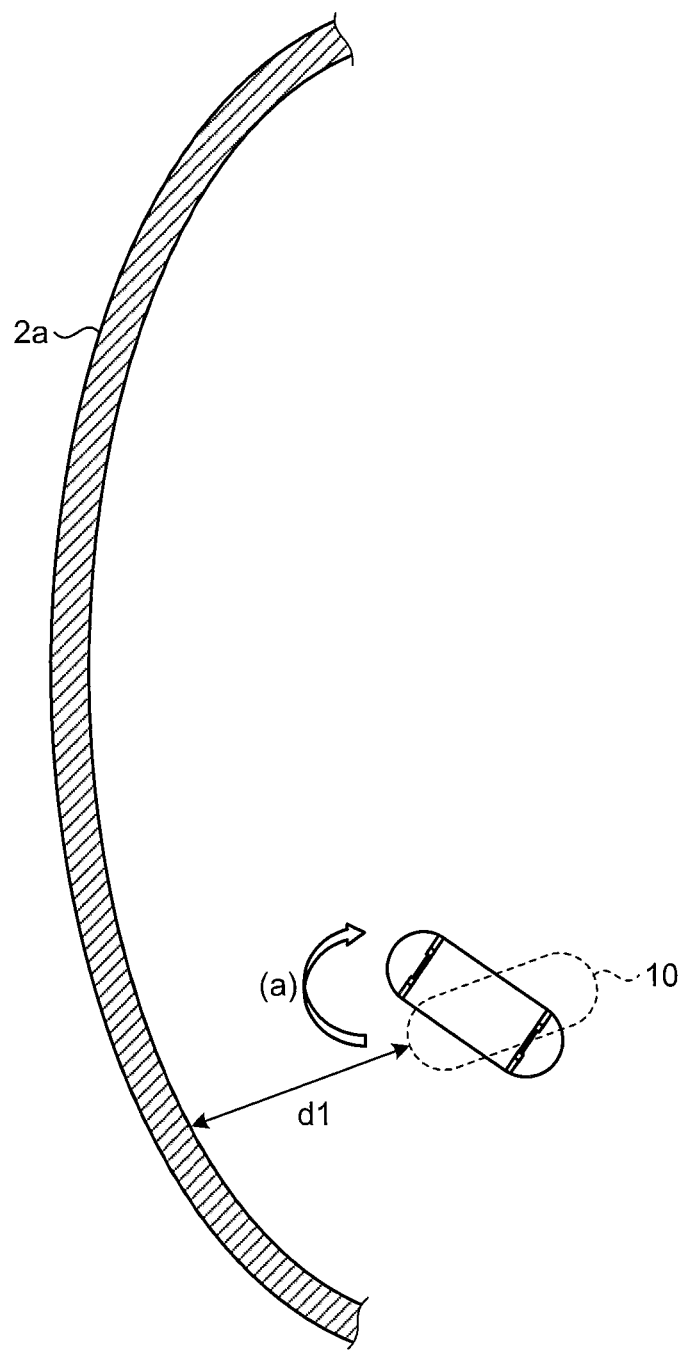
FIG. 7B is a diagram schematically illustrating a transition in the subject of the capsule endoscope according to the first modified example of the first embodiment of the present invention.
Figure 7C:
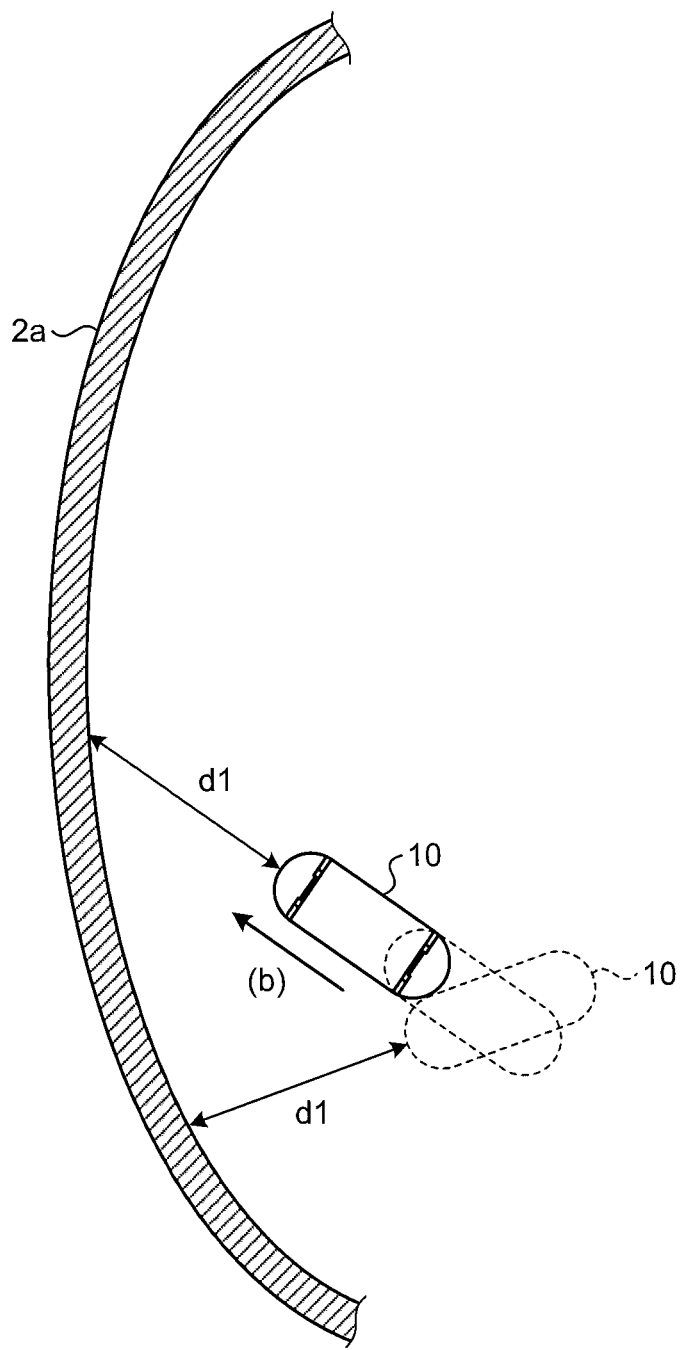
FIG. 7C is a diagram schematically illustrating a transition in the subject of the capsule endoscope according to the first modified example of the first embodiment of the present invention.
Figure 7D:
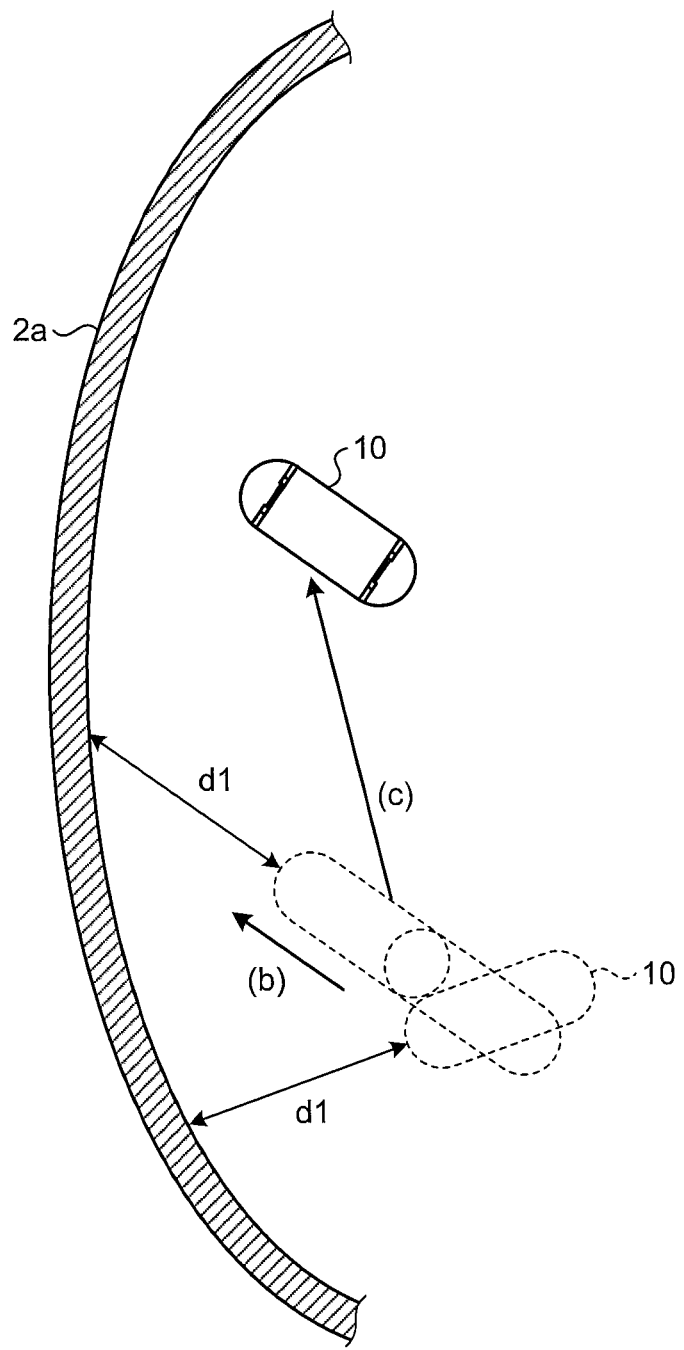
FIG. 7D is a diagram schematically illustrating a transition in the subject of the capsule endoscope according to the first modified example of the first embodiment of the present invention.
Figure 7E:
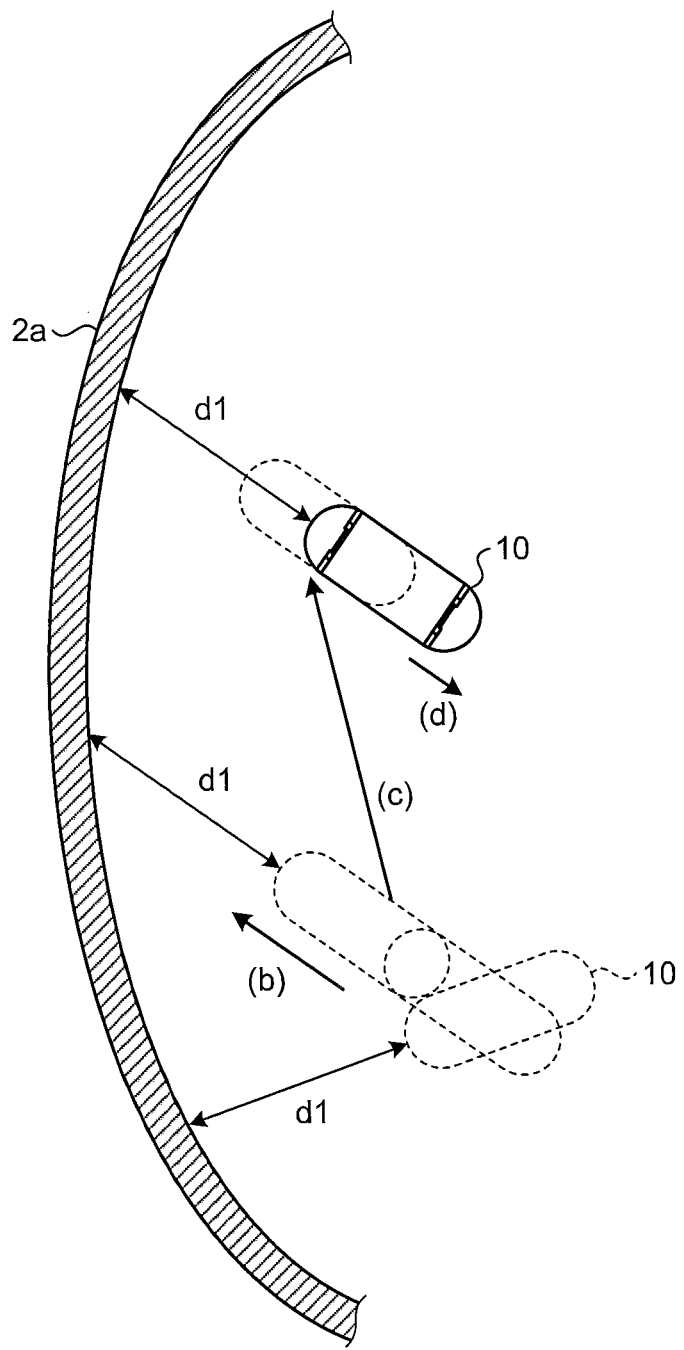
FIG. 7E is a diagram schematically illustrating a transition in the subject of the capsule endoscope according to the first modified example of the first embodiment of the present invention.
Figure 7F:
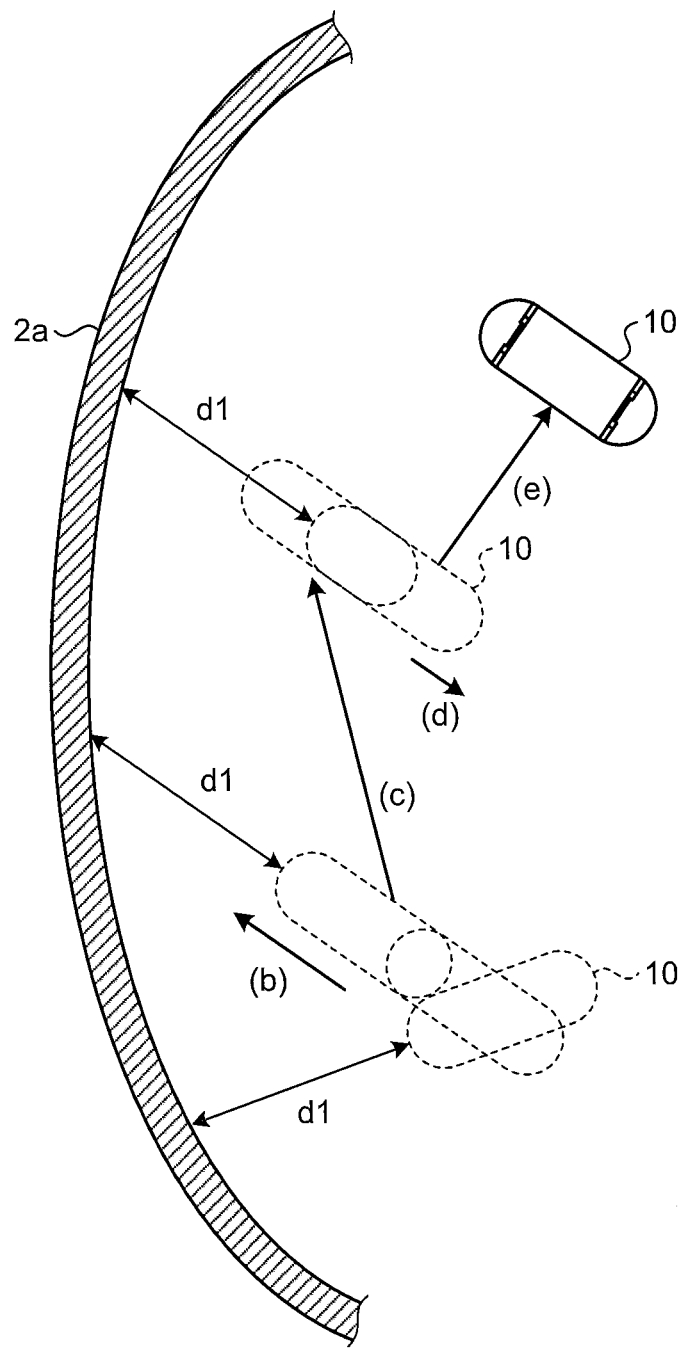
FIG. 7F is a diagram schematically illustrating a transition in the subject of the capsule endoscope according to the first modified example of the first embodiment of the present invention.
Figure 7G:
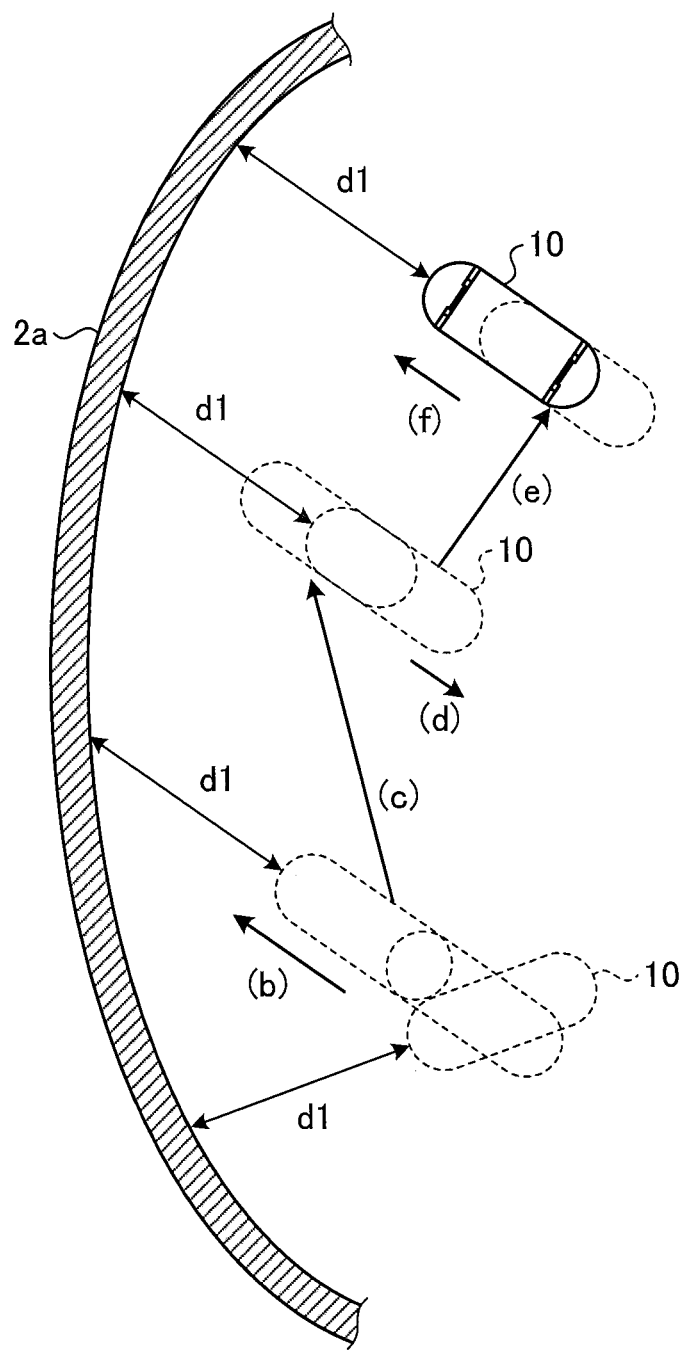
FIG. 7G is a diagram schematically illustrating a transition in the subject of the capsule endoscope according to the first modified example of the first embodiment of the present invention.

First, as illustrated in FIG. 7A, in a state in which the distance between the capsule endoscope 10 and the wall surface 2a of the subject 2 is maintained at the reference distance d1, when the command signal to rotate the capsule endoscope 10 rightward is inputted from the joystick 161, the magnetic field controller 174 causes the magnetic field generating unit 12 to generate a magnetic field to rotate the capsule endoscope 10 rightward (arrow (a)) and changes the posture of the capsule endoscope 10 (FIG. 7A→FIG. 7B).

Subsequently, the magnetic field controller 174 guides the capsule endoscope 10 so that the distance between the capsule endoscope 10 and the wall surface 2a of the subject 2 becomes equal to the reference distance d1 set by the setting unit 171 (FIG. 7B→FIG. 7C) by controlling the magnetic field generating unit 12 through the signal generating unit 14 and controlling the guiding magnetic field generated by the magnetic field generating unit 12 so that the capsule endoscope 10 moves in the imaging direction (arrow (b)), based on the distance from the capsule endoscope 10 to the wall surface 2a of the subject 2 which is calculated by the detection unit 172 and the reference distance d1 set by the setting unit 171.

Thereafter, when the command signal to move the capsule endoscope 10 obliquely upward is inputted from the joystick 162, the magnetic field controller 174 guides the capsule endoscope 10 obliquely upward (FIG. 7C→FIG. 7D) by controlling the guiding magnetic field generated by the magnetic field generating unit 12 so that the capsule endoscope 10 moves obliquely upward (arrow (c)) based on the distance from the capsule endoscope 10 to the wall surface 2a of the subject 2 which is calculated by the detection unit 172 and the reference distance d1 set by the setting unit 171.

Subsequently, the magnetic field controller 174 maintains the capsule endoscope 10 so that the distance between the capsule endoscope 10 and the wall surface 2a of the subject 2 becomes equal to the reference distance d1 set by the setting unit 171 (FIG. 7D→FIG. 7E) by controlling the guiding magnetic field generated by the magnetic field generating unit 12 so that the capsule endoscope 10 moves in a direction (arrow (d)) opposite to the imaging direction based on the distance from the capsule endoscope 10 to the wall surface 2a of the subject 2 which is calculated by the detection unit 172 and the reference distance d1 set by the setting unit 171.

Thereafter, when the command signal to move the capsule endoscope 10 in a direction perpendicular to the observation direction of the capsule endoscope 10 is inputted from the joystick 162, the magnetic field controller 174 controls the magnetic field generating unit 12 so that the capsule endoscope 10 moves in a direction (arrow (e)) perpendicular to the observation direction (FIG. 7E→FIG. 7F) based on the distance from the capsule endoscope 10 to the wall surface 2a of the subject 2 which is calculated by the detection unit 172 and the reference distance d1 set by the setting unit 171.

Subsequently, the magnetic field controller 174 maintains the capsule endoscope 10 so that the distance between the capsule endoscope 10 and the wall surface 2a of the subject 2 is equal to the reference distance d1 set by the setting unit 171 (FIG. 7F→FIG. 7G) by controlling the magnetic field generating unit 12 so that the capsule endoscope 10 moves in the imaging direction (arrow (f)) based on the distance from the capsule endoscope 10 to the wall surface 2a of the subject 2 which is calculated by the detection unit 172 and the reference distance d1 set by the setting unit 171.

According to the first modified example of the first embodiment, even when the command signal indicating a movement of the capsule endoscope 10 in an oblique direction or a command signal indicating a change of the posture (rotation) of the capsule endoscope 10 is inputted from the joystick 162, the magnetic field controller 174 maintains the distance between the capsule endoscope 10 and the wall surface 2a of the subject 2 at a constant level based on the distance from the capsule endoscope 10 to the wall surface 2a of the subject 2 which is calculated by the detection unit 172 and the reference distance set by the setting unit 171, so that it is possible to perform a higher level guiding operation, improve observation performance, and acquire an appropriate image at all times.

Second Modified Example of First Embodiment

Next, a second modified example of the first embodiment of the present invention will be described. The second modified example of the first embodiment has the same configuration as that of the capsule endoscope system 1 according to the first embodiment, and an image displayed on the display unit 18 is different from that in the first embodiment. The image displayed on the display unit according to the second modified example of the first embodiment will be described. The same elements as those of the capsule endoscope system 1 according to the first embodiment are denoted by the same reference signs, and the explanation thereof will not be repeated.

Figure 8:
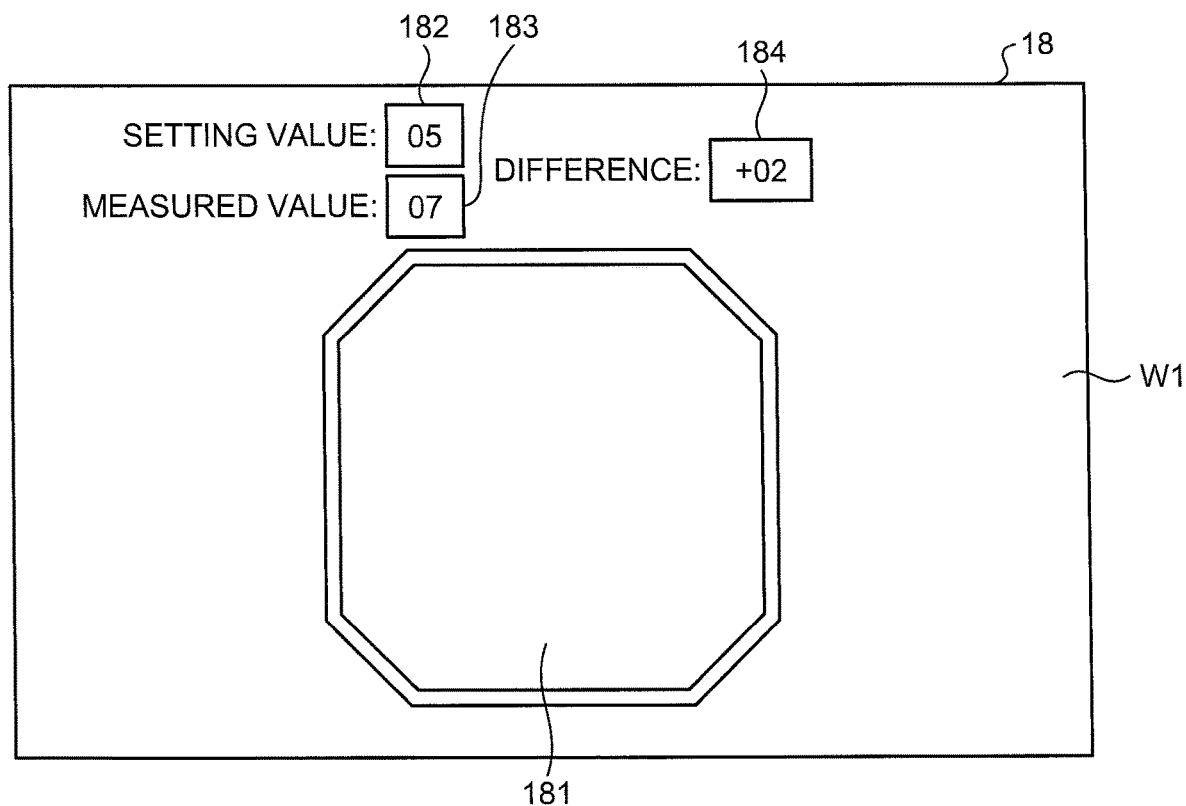
FIG. 8 is a diagram illustrating an example of an image displayed on a display unit according to a second modified example of the first embodiment of the present invention.

FIG. 8 is a diagram illustrating an example of an image displayed on a display unit according to the second modified example of the first embodiment of the present invention. As illustrated in FIG. 8, the display controller 175 causes the display unit 18 to display an image W1. The image W1 has an in-vivo image display area 181 that displays an in-vivo image of the subject 2 captured by the capsule endoscope 10, a setting display area 182 that displays a setting value where the distance between the capsule endoscope 10 and the subject 2 is set, a measured value display area 183 that displays an actual distance between the capsule endoscope 10 and the subject 2 which is calculated by the detection unit 172, and a difference display area 184 that displays a difference between the setting value and the measured value.

According to the second modified example of the first embodiment, the display controller 175 causes the display unit 18 to display the distance set by the setting unit 171, the distance calculated by the detection unit 172, the difference between the setting value and the measured value, and the in-vivo image captured by the capsule endoscope 10, so that a user can intuitively grasp whether or not an automatic guidance functions normally.

Further, according to the second modified example of the first embodiment, even when there is a time difference until the capsule endoscope 10 is guided and moved to the distance set by the setting unit 171, the movement can be visually grasped, so that it is possible to relieve stress of the user.

Further, in the second modified example of the first embodiment, the display controller 175 may control a display mode of a periphery of the in-vivo image display area 181 according to the difference between the setting value and the measured value. Specifically, the display controller 175 changes a color of a periphery (a frame) of the in-vivo image display area 181 based on the difference between the distance set by the setting unit 171 and the distance calculated by the detection unit 172. For example, the display controller 175 causes the display unit 18 to display the periphery of the in-vivo image display area 181 in red when the capsule endoscope 10 is becoming closer to the wall surface 2a of the subject 2 than the distance set by the setting unit 171, causes the display unit 18 to display the periphery of the in-vivo image display area 181 in blue when the capsule endoscope 10 is becoming farther from the wall surface 2a of the subject 2 than the distance set by the setting unit 171, and causes the display unit 18 to display the periphery of the in-vivo image display area 181 in green when the capsule endoscope 10 is approaching the distance set by the setting unit 171. Thereby, the user can intuitively grasp a distance relationship between the capsule endoscope 10 and the wall surface 2a of the subject 2. Further, the display controller 175 may cause the display unit 18 to display the in-vivo image by changing color strength and brightness of the in-vivo image according to the difference between the setting value and the measured value.

Third Modified Example of First Embodiment

Next, a third modified example of the first embodiment of the present invention will be described. The third modified example of the first embodiment has the same configuration as that of the capsule endoscope system 1 according to the first embodiment, and a setting method of the reference distance d1 to the lumen wall is different from that in the first embodiment. The setting method of the reference distance d1 to the lumen wall according to the third modified example of the first embodiment will be described. The same elements as those of the capsule endoscope system 1 according to the first embodiment are denoted by the same reference signs, and the explanation thereof will not be repeated.

In step S101 illustrated in FIG. 4, the setting unit 171 sets a result obtained by calculating the distance from the capsule endoscope 10 to the lumen wall surface of the subject 2 as the reference distance d1, based on an image generated by the capsule endoscope 10 when the joystick 162 is operated and on the light control information included in the image. In the third modified example of the first embodiment, the distance input unit 163 is not required in the configuration.

According to the third modified example of the first embodiment, after guiding the capsule endoscope 10 to an appropriate distance from the lumen wall surface of the subject 2, it is possible to guide the capsule endoscope 10 along the lumen wall surface while maintaining the above state, so that it is possible to realize high operability.

Further, in the third modified example of the first embodiment, a toggle switch (not illustrated in the drawings) that selects whether or not to control the distance to the lumen wall surface within a prescribed range may be included instead of the distance input unit 163, and the distance from the capsule endoscope 10 to the lumen wall surface of the subject 2 at a timing when the toggle switch is toggled (a timing to start controlling the distance to the lumen wall surface within a prescribed range) may be set as the reference distance d1. Thereby, it is possible to deal with a mode to control the distance to the lumen wall surface within a prescribed range and a mode not to control the distance by using the same input devices (the joysticks 161 and 162), so that the operability is improved.

Second Embodiment

Next, a second embodiment of the present invention will be described. A capsule endoscope system according to the second embodiment has a configuration different from that of the input unit 16 and the control unit 17 in the capsule endoscope system 1 according to the first embodiment. A configuration of the capsule endoscope system according to the second embodiment will be described, and thereafter processing performed by a control unit according to the second embodiment will be described. The same elements as those of the capsule endoscope system 1 according to the first embodiment are denoted by the same reference signs, and the explanation thereof will not be repeated.

Figure 9:
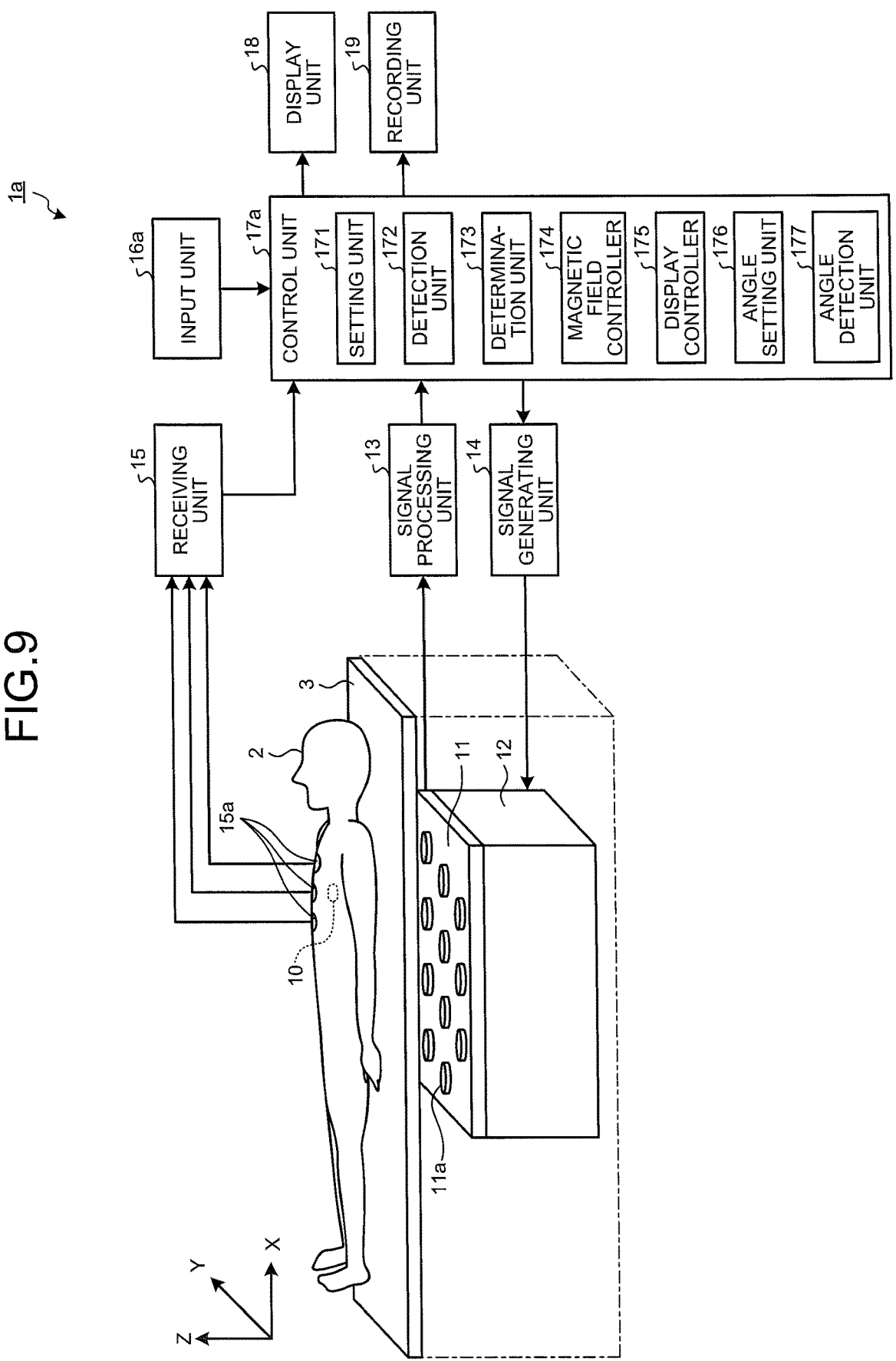
FIG. 9 is a diagram illustrating a configuration example of a capsule endoscope system according to a second embodiment of the present invention.

FIG. 9 is a diagram illustrating a configuration example of the capsule endoscope system according to the second embodiment of the present invention. A capsule endoscope system 1a illustrated in FIG. 9 includes an input unit 16a and a control unit 17a instead of the input unit 16 and the control unit 17 of the capsule endoscope system 1 according to the first embodiment.

Figure 10:
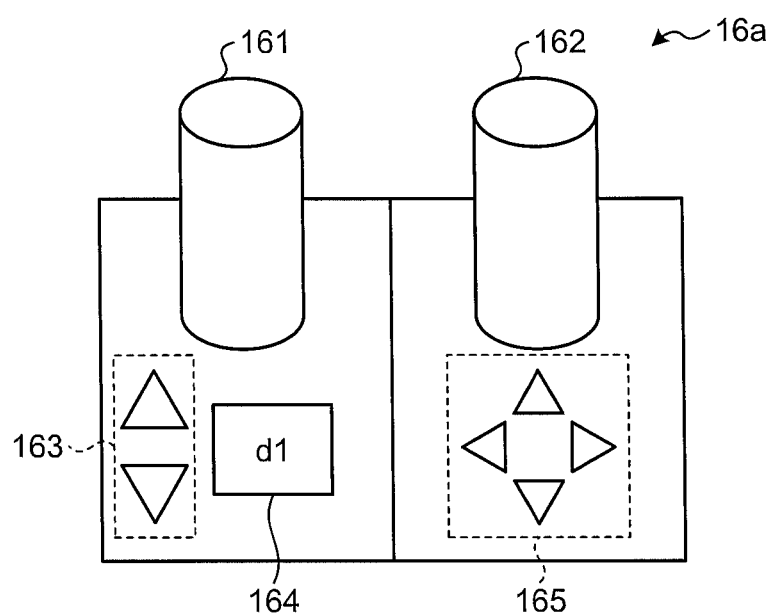
FIG. 10 is a schematic configuration diagram of an input unit according to the second embodiment of the present invention.

FIG. 10 is a schematic configuration diagram of the input unit 16a according to the second embodiment of the present invention. The input unit 16a illustrated in FIG. 10 has, in addition to a configuration of the input unit 16 according to the first embodiment, a posture setting unit 165 that receives an input of a command signal that sets an angle (posture) between the imaging direction of a capsule endoscope 10 and an imaging surface whose image is captured by the capsule endoscope 10. In the second embodiment, because it is difficult to detect a precise angle of the capsule endoscope 10, it is preferable that the number of angles that can be inputted to the posture setting unit 165 is three (−45 degrees, 0 degrees, and +45 degrees: 0 degrees when a wall surface 2a of a subject 2 is perpendicular to the imaging direction of the capsule endoscope 10) or five (−60 degrees, −45 degrees, 0 degrees, +45 degrees, and +60 degrees: 0 degrees when the wall surface 2a of the subject 2 is perpendicular to the imaging direction of the capsule endoscope 10).

The control unit 17a has an angle setting unit 176 and an angle detection unit 177 in addition to a configuration of the control unit 17 of the first embodiment.

The angle setting unit 176 sets a reference angle (posture) between the imaging direction of the capsule endoscope 10 and the imaging surface whose image is captured by the capsule endoscope 10 based on the command signal inputted from the posture setting unit 165.

The angle detection unit 177 calculates an angle between the imaging direction of the capsule endoscope 10 and the imaging surface whose image is captured by the capsule endoscope 10 based on a brightness distribution of an in-vivo image transmitted from the capsule endoscope 10.

Figure 11:
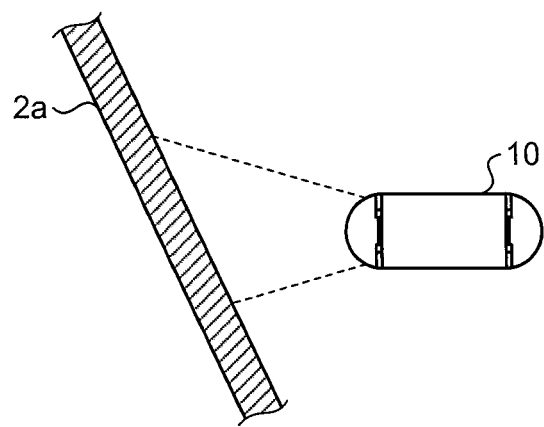
FIG. 11 is a diagram illustrating a relationship between a capsule endoscope according to the second embodiment of the present invention and a wall surface of a subject.
Figure 12:
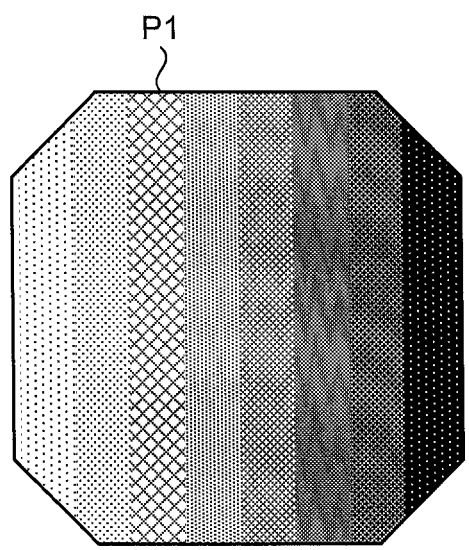
FIG. 12 is a diagram illustrating an example of an in-vivo image captured by the capsule endoscope under a condition illustrated in FIG. 11.

Next, a calculation method of the angle detection unit 177 will be described. FIG. 11 is a diagram illustrating a relationship between the capsule endoscope 10 and the wall surface 2a of the subject 2. FIG. 12 is a diagram illustrating an example of an in-vivo image captured by the capsule endoscope 10 under a condition illustrated in FIG. 11.

As illustrated in FIGS. 11 and 12, in a case in which the imaging direction of the capsule endoscope 10 is inclined with respect to the wall surface 2a of the subject 2, when the capsule endoscope 10 captures an image of the wall surface 2a of the subject 2, an in-vivo image P1 captured by the capsule endoscope 10 is an image in which the brightness varies according to a distance from the capsule endoscope 10 to the wall surface 2a of the subject 2. For example, as illustrated in FIG. 12, the greater the distance from the capsule endoscope 10 to the wall surface 2a of the subject 2, the smaller the amount of reflection light of the illumination light emitted from the illumination unit 114. Accordingly, the in-vivo image P1 gradually darkens according to the distance. Therefore, the angle detection unit 177 simulatively calculates the angle between the imaging direction of the capsule endoscope 10 and the imaging surface whose image is captured by the capsule endoscope 10, by detecting a ratio of brightness in the horizontal direction or the vertical direction in the in-vivo image transmitted from the capsule endoscope 10.

Processing of Capsule Endoscope System

Figure 13:
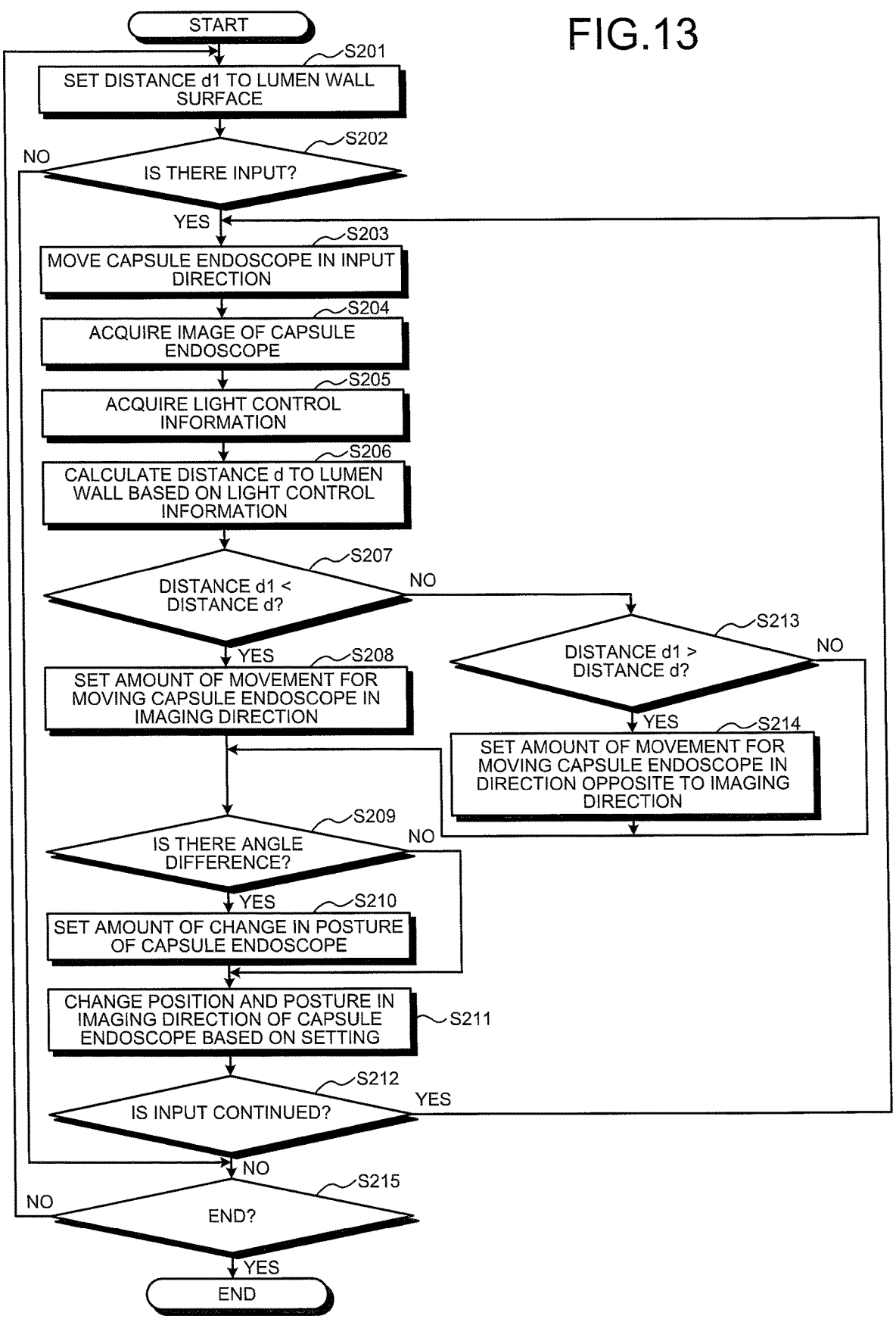
FIG. 13 is a flowchart illustrating an overview of processing performed by the capsule endoscope system according to the second embodiment of the present invention.

Next, processing performed by the capsule endoscope system 1a will be described. FIG. 13 is a flowchart illustrating an overview of the processing performed by the capsule endoscope system 1a.

In FIG. 13, steps S201 to S207 correspond to steps S101 to S107 in FIG. 4, respectively.

In step S208, the setting unit 171 sets the amount of movement for moving the capsule endoscope 10 in the imaging direction of the imaging unit 102.

Subsequently, a determination unit 173 determines whether or not there is a difference between an angle set by the angle setting unit 176 and an angle calculated by the angle detection unit 177 (step S209). When the determination unit 173 determines that there is a difference between the angle set by the angle setting unit 176 and the angle calculated by the angle detection unit 177 (step S209: Yes), the control unit 17a proceeds to step S210 described below. On the other hand, when the determination unit 173 determines that there is no difference between the angle set by the angle setting unit 176 and the angle calculated by the angle detection unit 177 (step S209: No), the control unit 17a proceeds to step S211 described below.

In step S210, the angle setting unit 176 sets the amount of change in the posture of the capsule endoscope 10. After step S210, the control unit 17a proceeds to step S211.

Subsequently, the magnetic field controller 174 controls the guiding magnetic field generated by the magnetic field generating unit 12 so as to change the position and the posture in the imaging direction of the capsule endoscope 10 based on the amount of movement set by the setting unit 171 and the amount of change set by the angle setting unit 176 (step S211). After step S211, the control unit 17a proceeds to step S212.

Steps S212 and S213 correspond to steps S109 to S110 in FIG. 4, respectively.

In step S214, the setting unit 171 sets the amount of movement for moving the capsule endoscope 10 in a direction opposite to the imaging direction of the imaging unit 102. After step S214, the control unit 17a proceeds to step S209.

Step S215 corresponds to step S112 in FIG. 4.

According to the second embodiment, the magnetic field controller 174 can move the capsule endoscope 10 while maintaining the distance from the capsule endoscope 10 to the wall surface 2a of the subject 2 at a set constant distance and can maintain a setting of the observation angle with respect to the wall surface 2a of the subject 2 at a constant angle. Therefore, it is possible to acquire a bird's-eye view of an in-vivo image.

Further, according to the second embodiment, it is possible to easily grasp a degree of unevenness of a torose lesion and the like in the subject 2. Therefore, it is possible to improve an observation performance on the subject 2.

First Modified Example of Second Embodiment

Next, a first modified example of the second embodiment of the present invention will be described. The first modified example of the second embodiment has the same configuration as that of the capsule endoscope system 1a of the second embodiment, and is different from the capsule endoscope system 1a according to the second embodiment in a setting method of an angle between the imaging direction of the capsule endoscope 10 and the imaging surface whose image is captured by the capsule endoscope 10. The setting method of the angle between the imaging direction of the capsule endoscope 10 and the imaging surface whose image is captured by the capsule endoscope 10 according to the first modified example of the second embodiment will be described. The same elements as those of the capsule endoscope system 1a according to the second embodiment are denoted by the same reference signs, and the explanation thereof will not be repeated.

The angle setting unit 176 sets an angle between the imaging direction of the capsule endoscope 10 and the imaging surface whose image is captured by the capsule endoscope 10 as a reference angle based on an image generated by the capsule endoscope 10 when the joystick 162 is operated. In the first modified example of the second embodiment, a posture setting unit 165 is not required in the configuration.

According to the first modified example of the second embodiment, after bringing the angle between the imaging direction of the capsule endoscope 10 and the imaging surface whose image is captured by the capsule endoscope 10 to an appropriate angle, it is possible to guide the capsule endoscope 10 along the lumen wall surface while maintaining the above state. Therefore, it is possible to realize high operability.

Further, in the first modified example of the second embodiment, a toggle switch (not illustrated in the drawings) that selects whether or not to control the angle between the imaging direction of the capsule endoscope 10 and the imaging surface whose image is captured by the capsule endoscope 10 within a prescribed range may be included instead of the posture setting unit 165. Accordingly, the angle between the imaging direction of the capsule endoscope 10 and the imaging surface whose image is captured by the capsule endoscope 10 at a timing when the toggle switch is toggled (a timing to start controlling the angle within a prescribed range) may be set as the reference angle. Thereby, it is possible to use a mode where the angle between the imaging direction of the capsule endoscope 10 and the imaging surface whose image is captured by the capsule endoscope 10 is controlled within a prescribed range and a mode where the angle is not controlled within a prescribed range, by using the same input device (the joystick 162). Therefore, the operability is improved.

Third Embodiment

Next, a third embodiment of the present invention will be described. A capsule endoscope system according to the third embodiment of the present invention has the same configuration as that of the capsule endoscope system 1a according to the second embodiment, and is different from the capsule endoscope system 1a according to the second embodiment in only the processing to be performed. Processing performed by the capsule endoscope system according to the third embodiment will be described. The same elements as those of the capsule endoscope system 1 according to the first embodiment are denoted by the same reference signs, and the explanation thereof will not be repeated.

Processing of Capsule Endoscope System

Figure 14:
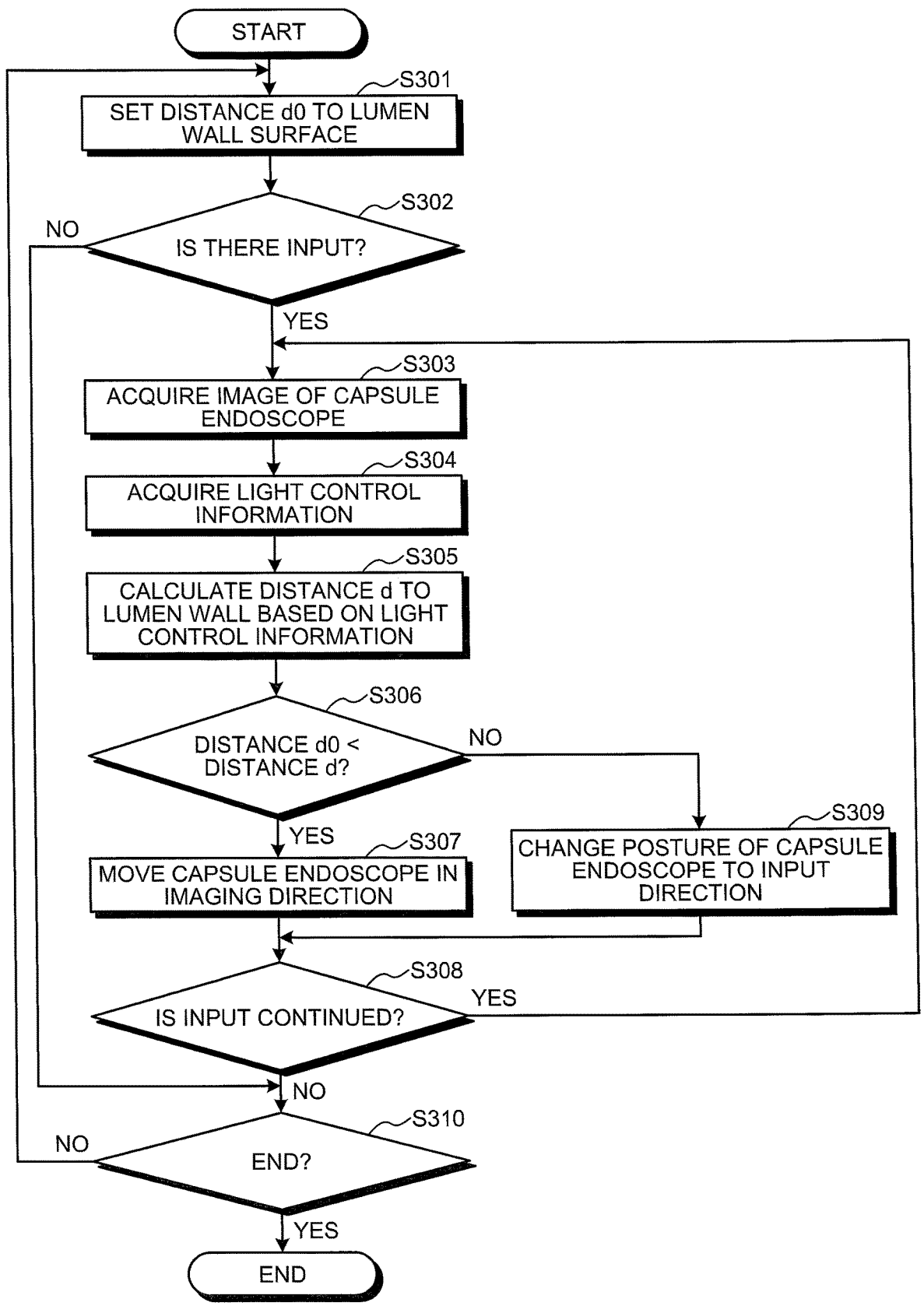
FIG. 14 is a flowchart illustrating an overview of processing performed by a capsule endoscope system according to a third embodiment of the present invention.

FIG. 14 is a flowchart illustrating an overview of the processing performed by a capsule endoscope system 1a according to the third embodiment of the present invention.

As illustrated in FIG. 14, first, a setting unit 171 sets a reference distance d0 from a capsule endoscope 10 to a lumen wall surface of a subject 2 based on the command signal inputted from a distance input unit 163 (step S301).

Steps S302 to S305 correspond to step S102 and steps S104 to S106 in FIG. 4, respectively.

In step S306, a determination unit 173 determines whether or not a distance d calculated by a detection unit 172 is greater than the reference distance d0 set by the setting unit 171 (d0<d). When the determination unit 173 determines that the distance d calculated by the detection unit 172 is greater than the reference distance d0 set by the setting unit 171 (step S306: Yes), a control unit 17a proceeds to step S307 described below. On the other hand, when the determination unit 173 determines that the distance d calculated by the detection unit 172 is not greater than the reference distance d0 set by the setting unit 171 (step S306: No), the control unit 17a proceeds to step S309 described below.

Figure 15A:
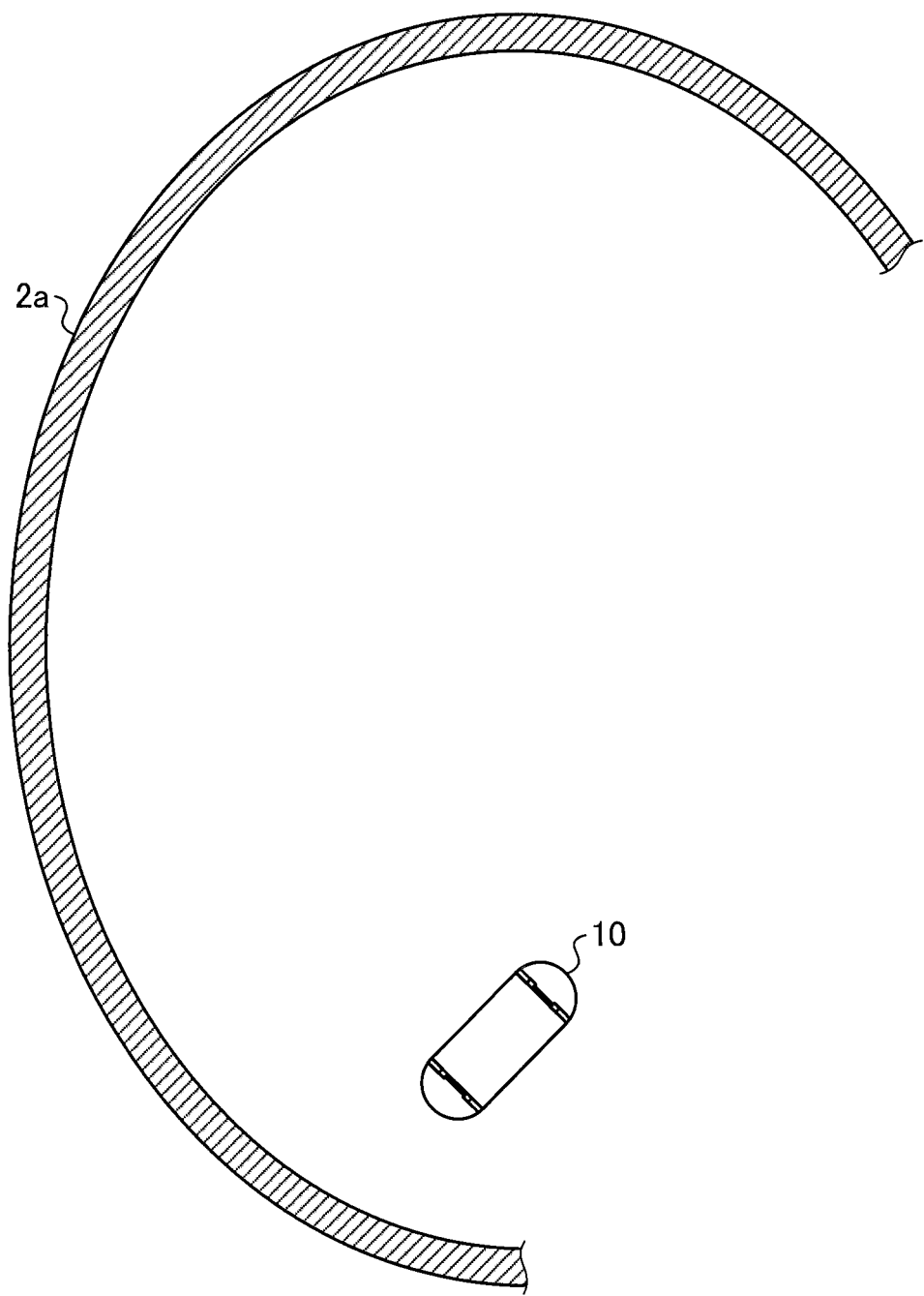
FIG. 15A is a diagram schematically illustrating a transition in a subject of the capsule endoscope according to the third embodiment of the present invention.
Figure 15B:
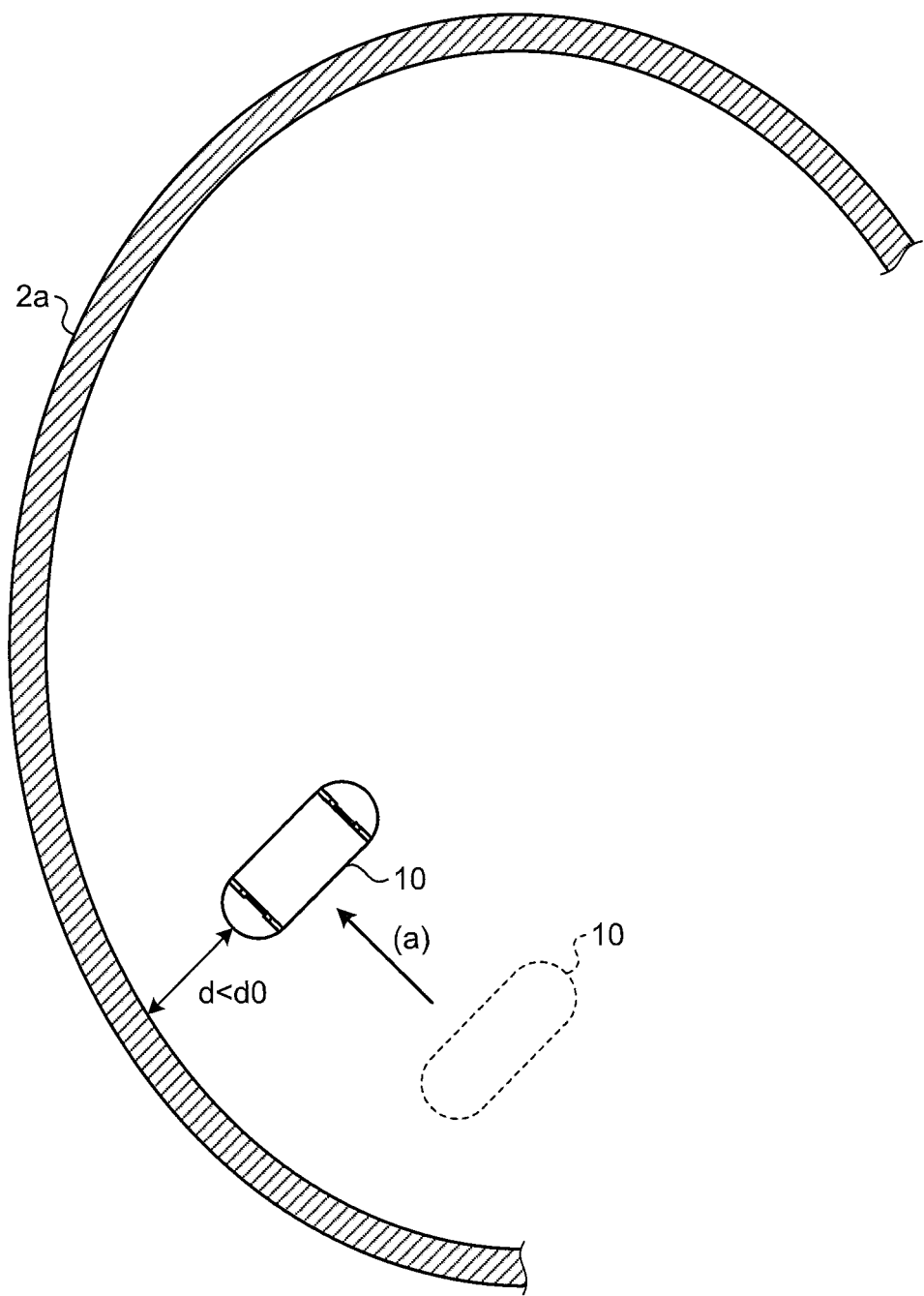
FIG. 15B is a diagram schematically illustrating a transition in the subject of the capsule endoscope according to the third embodiment of the present invention.

In step S307, a magnetic field controller 174 controls the guiding magnetic field generated by a magnetic field generating unit 12 so that the capsule endoscope 10 moves according to the command signal from a joystick 162 to instruct a movement of the capsule endoscope 10. Specifically, as illustrated in FIGS. 15A and 15B, the magnetic field controller 174 controls the guiding magnetic field generated by the magnetic field generating unit 12 so that the capsule endoscope 10 moves in an arrow (a) direction according to the command signal from the joystick 162 to instruct a movement of the capsule endoscope 10. After step S307, the control unit 17a proceeds to step S308 described below.

Figure 15C:
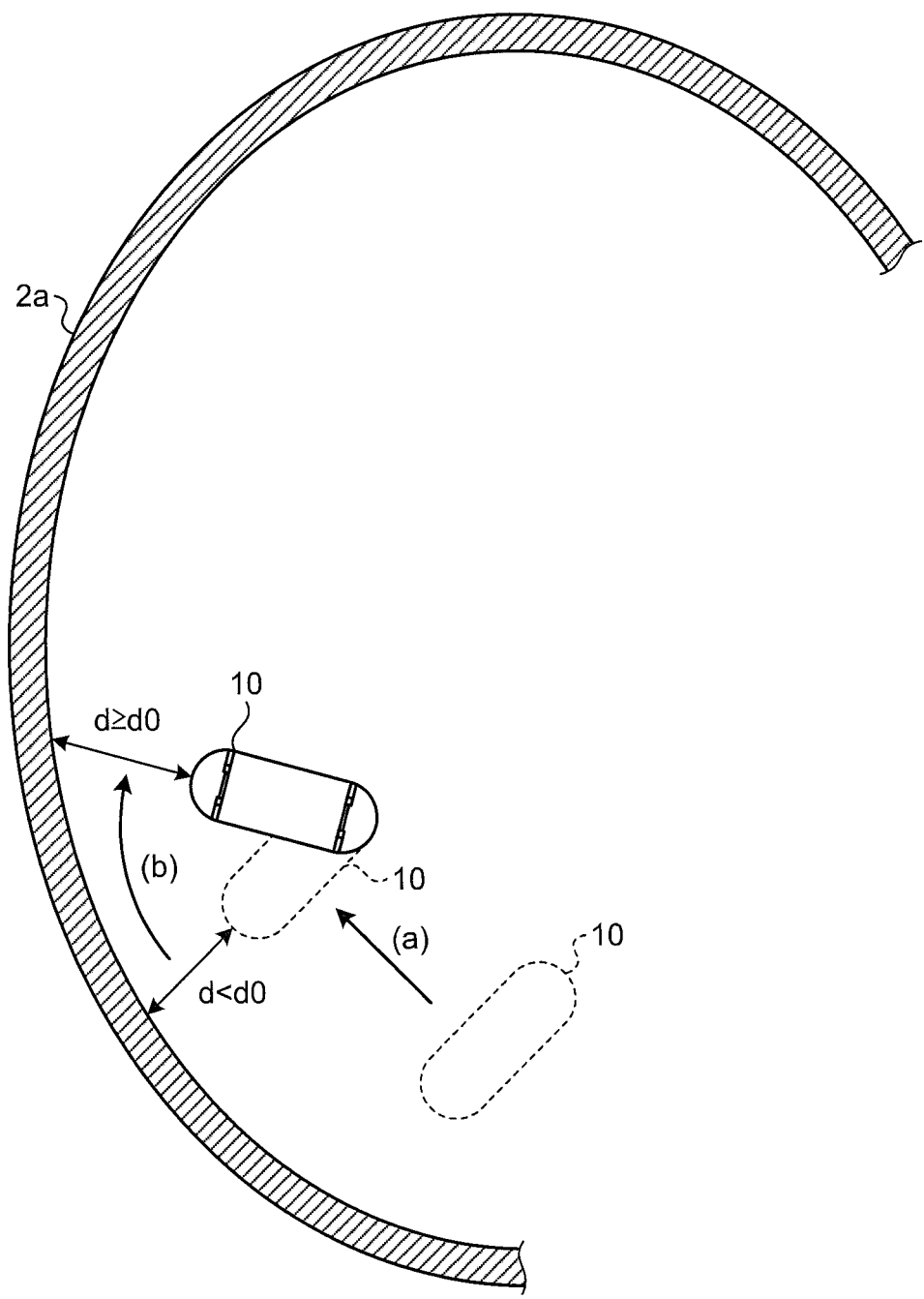
FIG. 15C is a diagram schematically illustrating a transition in the subject of the capsule endoscope according to the third embodiment of the present invention.

In step S309, the distance d calculated by the detection unit 172 is smaller than the reference distance d0 set by the setting unit 171 (d<d0), so that the magnetic field controller 174 controls the guiding magnetic field generated by the magnetic field generating unit 12 so as to change the posture of the capsule endoscope 10 to the input direction illustrated by an arrow (b) according to the command signal from the joystick 162 to instruct a movement of the capsule endoscope 10. Specifically, as illustrated in FIGS. 15B and 15C, the magnetic field controller 174 controls the guiding magnetic field generated by the magnetic field generating unit 12 so as to change the posture of the capsule endoscope 10 to the input direction according to the command signal from the joystick 162 to instruct a movement of the capsule endoscope 10. Thereby, it is possible to automatically switch the degree of freedom to move the capsule endoscope 10 with respect to an input in the vertical direction to the joystick 162 according to the distance between the capsule endoscope 10 and the wall surface 2a of the subject 2. After step S309, the control unit 17a proceeds to step S308 described below.

Figure 15D:
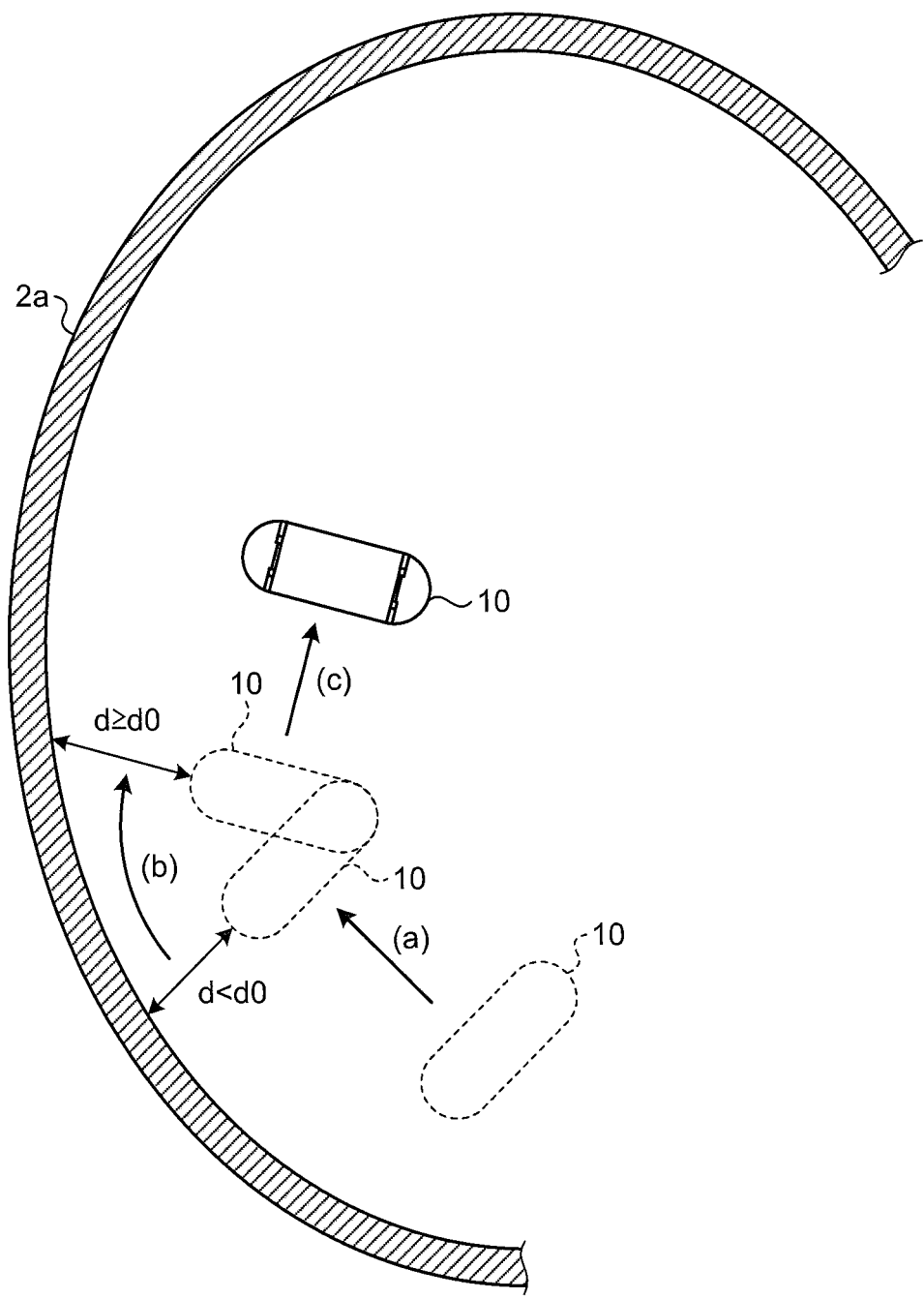
FIG. 15D is a diagram schematically illustrating a transition in the subject of the capsule endoscope according to the third embodiment of the present invention.
Figure 15E:
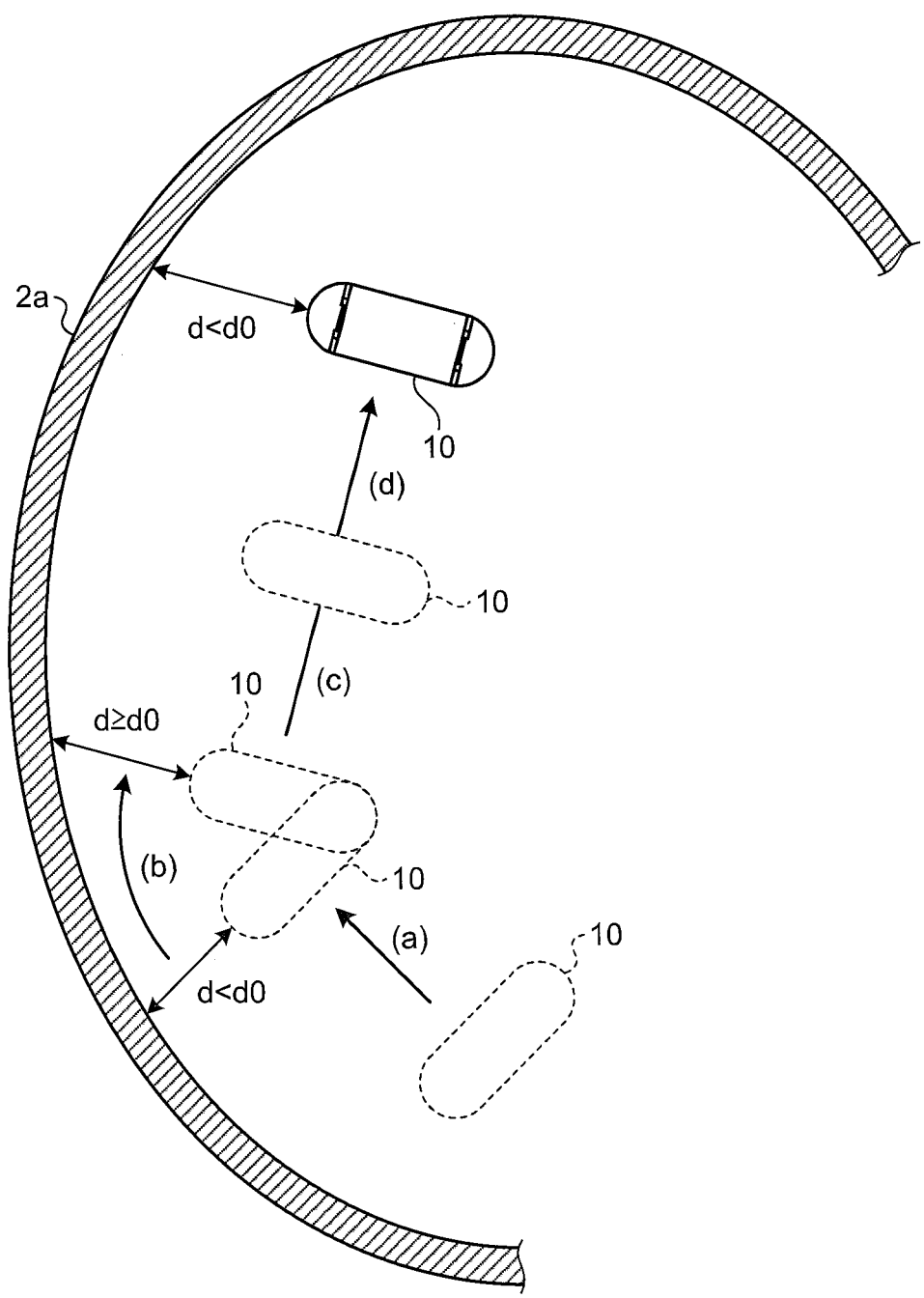
FIG. 15E is a diagram schematically illustrating a transition in the subject of the capsule endoscope according to the third embodiment of the present invention.
Figure 15F:
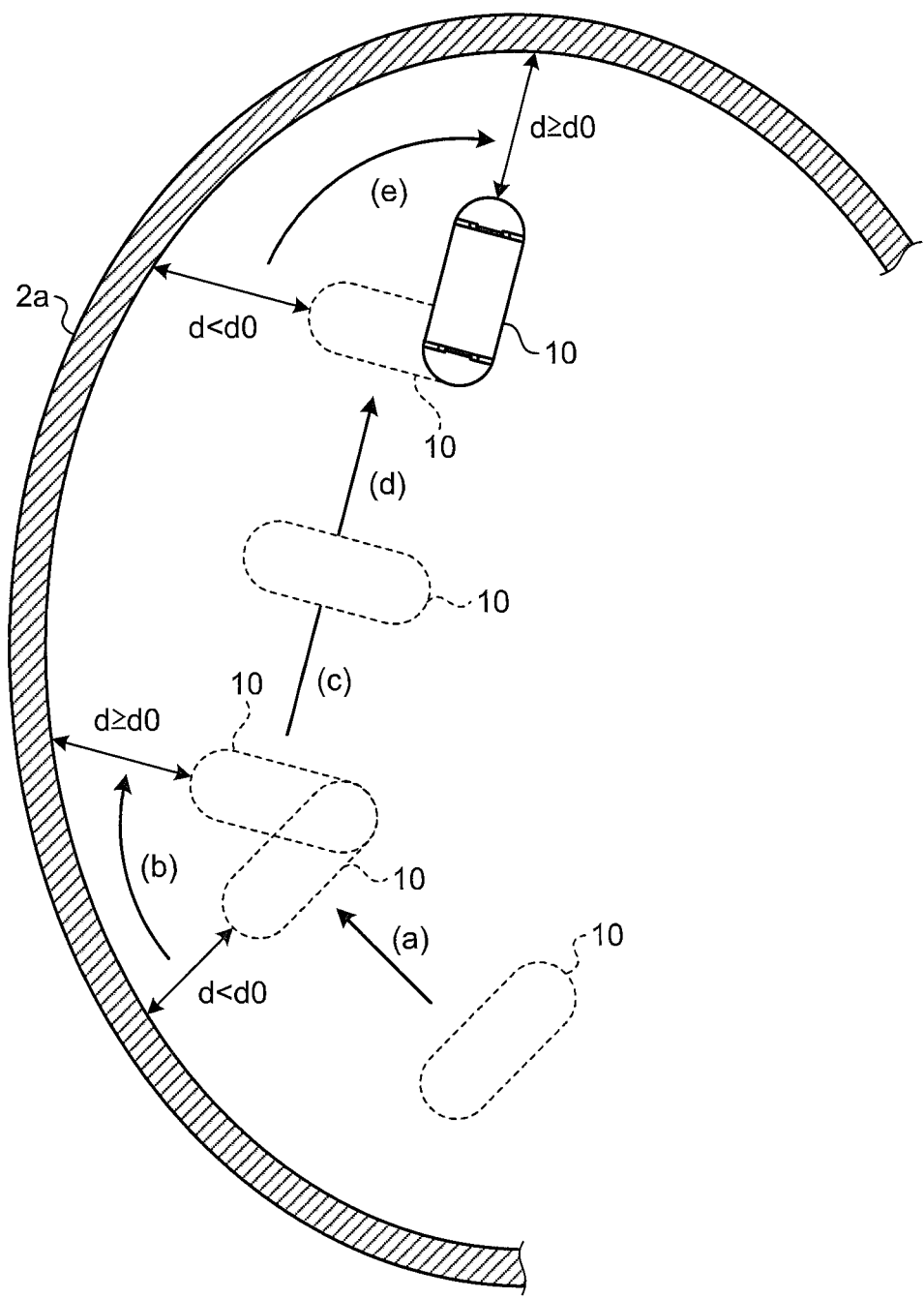
FIG. 15F is a diagram schematically illustrating a transition in the subject of the capsule endoscope according to the third embodiment of the present invention.
Figure 15G:
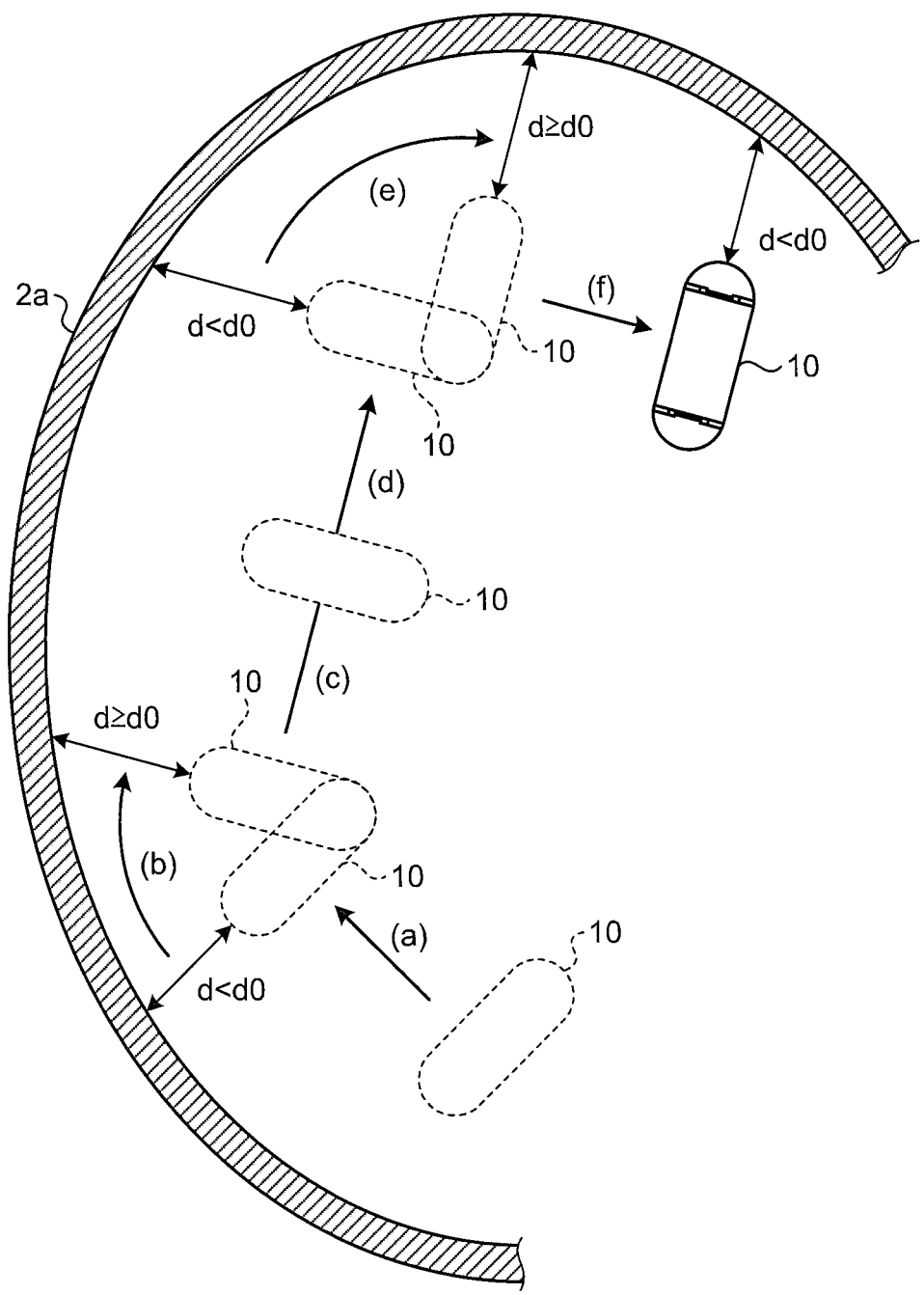
FIG. 15G is a diagram schematically illustrating a transition in the subject of the capsule endoscope according to the third embodiment of the present invention.

Subsequently, when the input of the command signal from the joystick 162 to instruct a movement of the capsule endoscope 10 is continued (step S308: Yes), the control unit 17a returns to step S303 and repeats the processing of steps S303 to S308. In this case, as illustrated in FIGS. 15C to 15E, when the distance d calculated by the detection unit 172 is greater than or equal to the reference distance d0 set by the setting unit 171 (d≥d0), the magnetic field controller 174 controls the guiding magnetic field generated by the magnetic field generating unit 12 so that the capsule endoscope 10 moves in an arrow (c) direction and an arrow (d) direction according to the command signal from the joystick 162 to instruct a movement of the capsule endoscope 10. Thereafter, as illustrated in FIGS. 15E and 15F, when the distance d calculated by the detection unit 172 becomes smaller than the reference distance d0 set by the setting unit 171 (d<d0), the magnetic field controller 174 controls the guiding magnetic field generated by the magnetic field generating unit 12 so as to change the posture of the capsule endoscope 10 to the input direction illustrated by an arrow (e) according to the command signal from the joystick 162 to instruct a movement of the capsule endoscope 10. Then, as illustrated in FIGS. 15F and 15G, when the distance d calculated by the detection unit 172 becomes greater than or equal to the reference distance d0 set by the setting unit 171 (d≥d0), the magnetic field controller 174 controls the guiding magnetic field generated by the magnetic field generating unit 12 so that the capsule endoscope 10 moves in an arrow (f) direction according to the command signal from the joystick 162 to instruct a movement of the capsule endoscope 10.

In step S308, when the input of the command signal from the joystick 162 to instruct the movement of the capsule endoscope 10 is not continued (step S308: No), the control unit 17a proceeds to step S310 described below.

Step S310 corresponds to step S112 in FIG. 4.

According to the third embodiment, when the distance d calculated by the detection unit 172 is smaller than the reference distance d0 set by the setting unit 171 (d<d0), the magnetic field controller 174 changes the posture of the capsule endoscope 10 to the input direction according to the command signal from the joystick 162 to instruct the movement of the capsule endoscope 10. On the other hand, when the distance d calculated by the detection unit 172 is greater than or equal to the reference distance d0 set by the setting unit 171 (d≥d0), the magnetic field controller 174 moves the position of the capsule endoscope 10 in the input direction according to the command signal from the joystick 162 to instruct the movement of the capsule endoscope 10. As a result, it is possible to switch the degree of freedom of position change and posture change of the capsule endoscope 10 for the joystick 162 according to the distance between the capsule endoscope 10 and the wall surface 2a of the subject 2.

Further, according to the third embodiment, when a user moves the position of the capsule endoscope 10 by operating the joystick 162 while viewing an in-vivo image displayed on the display unit 18, the posture of the capsule endoscope 10 is changed before the capsule endoscope 10 is too close to the wall surface 2a of the subject 2 even if the capsule endoscope 10 is continuously moved in the vertical direction. Therefore, it is possible to prevent the capsule endoscope 10 from coming into contact with the wall surface 2a of the subject 2. As a result, it is possible to smoothly continue the observation of the subject 2.

Further, in the third embodiment, the magnetic field controller 174 may change a percentage to move the capsule endoscope 10 in a direction perpendicular to the imaging direction of the capsule endoscope 10 corresponding to the command signal inputted from the input unit 16a and a percentage to change the posture of the capsule endoscope 10 with respect to the object, respectively, based on a ratio between the distance detected by the detection unit 172 and the reference distance set by the setting unit 171. In this case, the magnetic field controller 174 increases the percentage to change the posture of the capsule endoscope 10 as the distance detected by the detection unit 172 decreases. As a result, it is possible to switch the degree of freedom of position change and posture change of the capsule endoscope 10 for the joystick 162 according to the distance between the capsule endoscope 10 and the wall surface 2a of the subject 2 and it is possible to smoothly observe the subject 2 while preventing the capsule endoscope 10 from coming into contact with the wall surface 2a of the subject 2.

Other Embodiments

In the embodiments of the present invention, the detection unit 172 and the angle detection unit 177 detect the distance from the subject 2 to the capsule endoscope 10 and the angle between the subject 2 and the capsule endoscope 10 as spatial relationships around the capsule endoscope 10 based on the image data generated by the image sensor 116 of the capsule endoscope 10. However, for example, the control unit 107 of the capsule endoscope 10 may calculate the distance and the angle based on the image data generated by the image sensor 116. Further, a detection unit that detects the distance by using an ultrasonic wave may be provided in the capsule endoscope 10 and the detection unit may superimpose a detection result on the image data and transmit the image data to the outside.

In the description of the flowcharts herein, the anteroposterior relationship of the processing steps is described by using the terms such as "first", "thereafter", and "subsequently". However, the sequence of the processing steps necessary to implement the present invention is not uniquely determined by these terms. That is to say, it is possible to change the sequence of the processing steps in the flowcharts described herein within a range without inconsistency.

The present invention is not limited to the above embodiments as they are, and the invention can be embodied with its elements modified in an implementation phase without departing from the scope of the invention. Further, various inventions can be formed by appropriately combining a plurality of elements disclosed in the above embodiments. For example, some elements, among all the elements stated in the embodiments, may be deleted without departing from the scope of the present invention. Furthermore, the elements over different embodiments may be appropriately combined.

A term stated at least once along with a different term with broader or the same meaning in the specification or the drawings can be replaced by the different term in any part of the specification or the drawings. In this way, various modifications and applications are possible without departing from the scope of the invention.

According to some embodiments, it is possible to improve the operability to guide the capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope system comprising:
   a capsule endoscope configured to be introduced into a subject and having an imaging sensor configured to image an object to generate an image of the object;
   a magnetic field generator configured to generate the magnetic field to guide the capsule endoscope; and
   a controller configured to:
      receive commands for changing at least one of a position and a posture of the capsule endoscope;
      set a reference distance between the imaging sensor and the object;
      receive a detected distance between the object and the imaging sensor;
      determine a relationship between the reference distance and the detected distance based on the position and the posture changed in response to the received commands; and
      control the magnetic field generator to generate the magnetic field so as to:
         guide the capsule endoscope toward a direction of the object when the detected distance is larger than the reference distance;
         guide the capsule endoscope away from the object when the reference distance is larger than the detected distance; and
         hold the capsule endoscope at the position when the reference distance is equal to the detected distance.

2. The capsule endoscope system according to claim 1, wherein the distance is detected based on brightness of the image.

3. The capsule endoscope system according to claim 1, wherein when the commands for changing the posture of the capsule endoscope are received, the controller is configured to control the magnetic field generator to generate the magnetic field so as to change the posture of the capsule endoscope with respect to the object while the difference is maintained within a certain range.

4. The capsule endoscope system according to claim 1, wherein the controller is configured to control the magnetic field generator to generate the magnetic field based on a ratio between the distance and the reference distance so as to change each of a percentage to move the capsule endoscope in a direction perpendicular to an imaging direction of the imaging sensor and a percentage to change the posture of the capsule endoscope with respect to the object.

5. The capsule endoscope system according to claim 4, wherein the controller is configured to increase the percentage to change the posture of the capsule endoscope as the distance decreases.

6. The capsule endoscope system according to claim 1, wherein
when the distance is greater than or equal to the reference distance, the controller is configured to control the magnetic field generator to generate the magnetic field such that the capsule endoscope moves in a direction perpendicular to an imaging direction of the imaging sensor, and
when the distance is smaller than the reference distance, the controller is configured to control the magnetic field generator to generate the magnetic field so as to change the posture of the capsule endoscope with respect to the object.

7. The capsule endoscope system according to claim 1, wherein the controller is further configured to display each of the image and the difference.

8. The capsule endoscope system according to claim 7, wherein the controller is further configured to change a display mode of the image according to the difference.

9. The capsule endoscope system according to claim 1, wherein the controller is further configured to:
set a reference angle between an imaging direction of the imaging sensor and the object,
receive a detected angle between the imaging direction of the imaging sensor and the object, and
control the magnetic field generator to generate the magnetic field such that a difference between the angle and the reference angle is maintained within a certain range.

10. The capsule endoscope system according to claim 9, wherein when the commands for changing the position of the capsule endoscope are received, the controller is configured to control the magnetic field generator to generate the magnetic field such that the capsule endoscope moves in a direction perpendicular to the imaging direction of the imaging sensor while the difference is maintained within the certain range.

11. The capsule endoscope system according to claim 10, wherein the controller is configured to control the magnetic field generator to generate the magnetic field based on the angle and the reference angle such that the posture of the capsule endoscope changes with the angle being orthogonal to the reference angle.

12. The capsule endoscope system according to claim 1, wherein the controller is further configured to:
set a reference angle between an imaging direction of the imaging sensor and the object,
receive the detected distance and a detected angle between the imaging direction of the imaging sensor and the object, based on brightness of the image, and
control the magnetic field generator to generate the magnetic field such that the capsule endoscope moves in a direction perpendicular to the imaging direction of the imaging sensor while the difference between the distance and the reference distance is maintained within a first certain range and a difference between the angle and the reference angle is maintained within a second certain range.

13. A magnetic field generating device for guiding a capsule endoscope, the capsule endoscope being configured to be introduced into a subject and having an imaging sensor configured to image an object to generate an image of the object, the magnetic field generating device comprising:
a magnetic field generator configured to generate the magnetic field to guide the capsule endoscope; and
a controller configured to:
receive commands for changing at least one of a position and a posture of the capsule endoscope;
set a reference distance between the imaging sensor and the object;
receive a detected distance between the object and the imaging sensor;
determine a relationship between the reference distance and the detected distance based on the position and the posture changed in response to the received commands; and
control the magnetic field generator to generate the magnetic field so as to:
guide the capsule endoscope toward a direction of the object when the detected distance is larger than the reference distance;
guide the capsule endoscope away from the object when the reference distance is larger than the detected distance; and
hold the capsule endoscope at the position when the reference distance is equal to the detected distance.

* * * * *